(12) United States Patent
Kim

(10) Patent No.: US 11,775,698 B2
(45) Date of Patent: Oct. 3, 2023

(54) METHOD, SERVER AND COMPUTER PROGRAM FOR DESIGNING CUSTOMIZED HEADGEAR FOR TRANSCRANIAL DIRECT CURRENT STIMULATION

(71) Applicant: NEUROPHET Inc., Seoul (KR)

(72) Inventor: Dong Hyeon Kim, Seoul (KR)

(73) Assignee: NEUROPHET Inc., Seoul (KR)

( * ) Notice: Subject to any disclaimer, the term of this patent is extended or adjusted under 35 U.S.C. 154(b) by 0 days.

(21) Appl. No.: 17/810,255

(22) Filed: Jun. 30, 2022

(65) Prior Publication Data

US 2023/0016807 A1 Jan. 19, 2023

(30) Foreign Application Priority Data

Jul. 6, 2021 (KR) .......................... 10-2021-0088248

(51) Int. Cl.
*A61N 1/04* (2006.01)
*G06F 30/10* (2020.01)

(52) U.S. Cl.
CPC ............ *G06F 30/10* (2020.01); *A61N 1/0456* (2013.01); *A61N 1/0472* (2013.01)

(58) Field of Classification Search
CPC ... A61N 1/0526; A61N 1/0472; A61N 1/0456
See application file for complete search history.

(56) References Cited

U.S. PATENT DOCUMENTS

| 2018/0160933 | A1 | 6/2018 | Urman et al. |
| 2019/0059732 | A1 | 2/2019 | Kim et al. |
| 2021/0268266 | A1* | 9/2021 | Hampstead .......... A61N 1/0484 |

FOREIGN PATENT DOCUMENTS

| KR | 10-2017-0047056 A | 5/2017 |
| KR | 10-2020-0138111 A | 12/2020 |

OTHER PUBLICATIONS

Mansouri, Farrokh et al. "Development and validation of a 3D-printed neuronavigation headset for therapeutic brain stimulation." Journal of Neural Engineering, <https://doi.org/10.1088/1741-2552/aacb96> Jun. 27, 2018.
Extended European Search Report for EP22183046.6 by European Patent Office dated Nov. 18, 2022.

* cited by examiner

*Primary Examiner* — Alyssa M Alter
(74) *Attorney, Agent, or Firm* — BROADVIEW IP LAW, PC

(57) ABSTRACT

Provided are a method, server, and computer program for designing a customized headgear for transcranial direct current stimulation. According to one embodiment, there is provided a method for designing a customized headgear for transcranial direct current stimulation performed by a computing device and applying electrical stimulation to a preset target point in a brain of a subject, the method including: acquiring a head image of the subject; generating a headgear mask by using the acquired head image; generating a stimulator mask by using an optimal stimulation position combination for applying the electrical stimulation to the preset target point; and generating a customized headgear mask for the subject by performing a subtraction operation between the generated headgear mask and the generated stimulator mask.

11 Claims, 17 Drawing Sheets

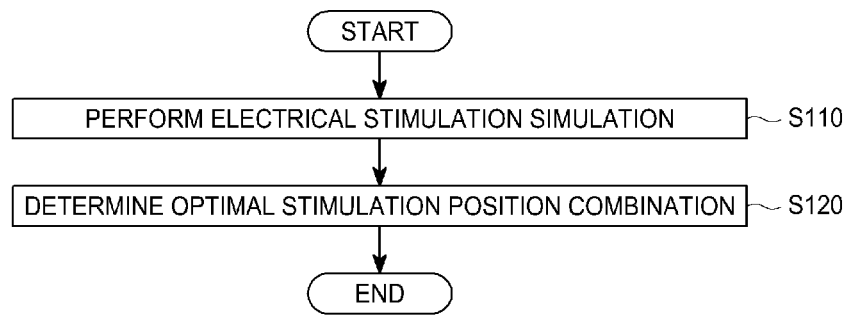
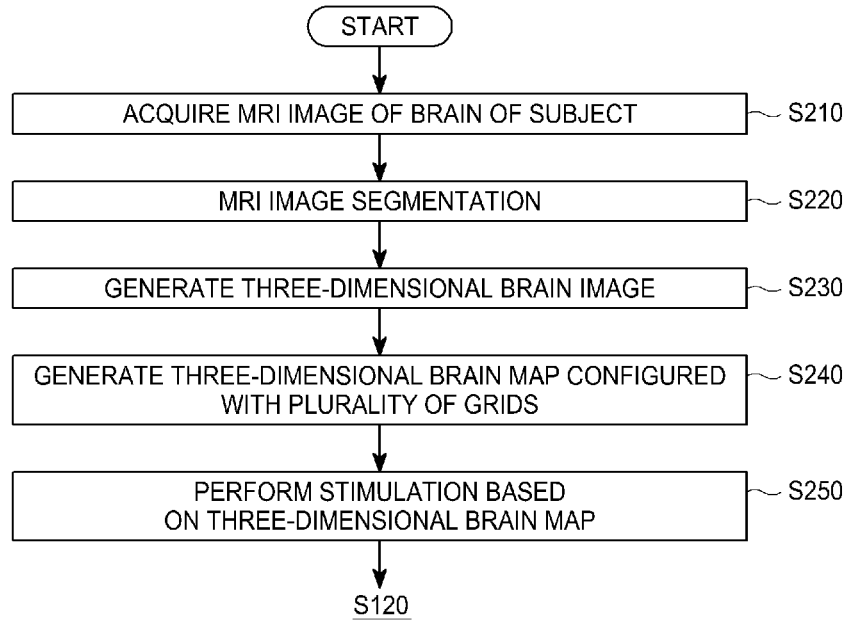

FIG. 5
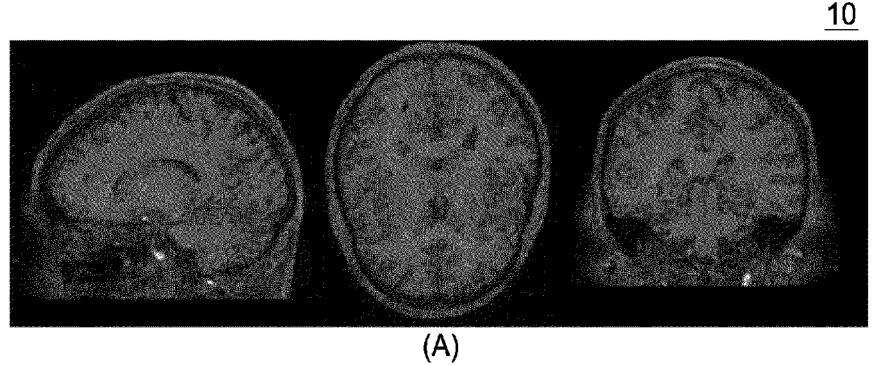
(A)
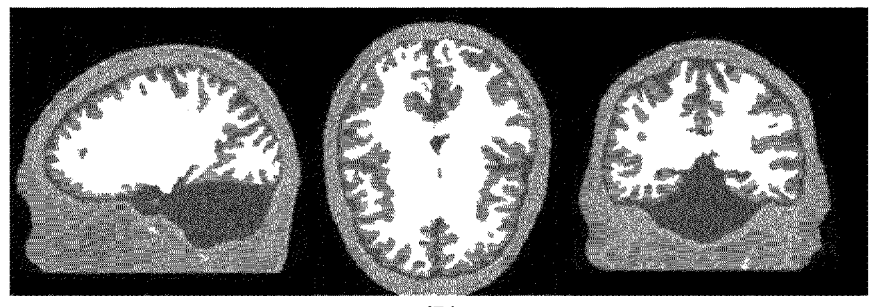
(B)

Optimization Report

[Conditions]
Target p[timize quantity : Enorm
Electrede max number : 8
Electrede shape : Disc 1 cm^2
Maximum current L 2.000

Target 1, Position : 279.30, 2.79, 327.86, Quantity amplitude : 0.104

[Result electrodes by 10-20 based optimization calculation]
Electrode 1 : Iz, Position : 256.97, -93.62, 347.00, amplitude : -0.800 mA
Electrode 2 : T9, Position : 178.25, 4.77, 348.96, amplitude : 0.100 mA
Electrode 3 : FT8, Position : 338.49, 32.90, 308.22, amplitude : -0.700 mA
Electrode 4 : P8, Position : 327.87, -53.02, 311.04, amplitude : -0.200 mA
Electrode 5 : F9, Position : 186.98, -63.16, 344.55, amplitude : 0.400 mA
Electrode 6 : FT9, Position : 180.82, 34.78, 347.25, amplitude : -0.300 mA
Electrode 7 : TP9, Position : 174.69, -20.29, 350.53, amplitude : 0.700 mA
Electrode 8 : F10, Position : 328.71, 62.43, 341.10, amplitude : 0.800 mA

METHOD, SERVER AND COMPUTER PROGRAM FOR DESIGNING CUSTOMIZED HEADGEAR FOR TRANSCRANIAL DIRECT CURRENT STIMULATION

CROSS-REFERENCE TO RELATED APPLICATION

This application claims priority under 35 U.S.C § 119 to Korean Patent Application No. 10-2021-0088248 filed in the Korean Intellectual Property Office on Jul. 6, 2021, the entire contents of which are hereby incorporated by reference.

FIELD OF THE INVENTION

Various embodiments of the present invention relate to the method, the server, and the computer program for designing the customized headgear for transcranial direct current stimulation in which the electrical stimulation is applied to the preset target point in the brain of the subject.

DESCRIPTION OF THE RELATED ART

The brain is an internal organ of the human head and is the highest central organ of the nervous system and is segmented into cerebrum, cerebellum, midbrain, pons, and medulla oblongata. In addition, the brain generates the brain wave which is a signal obtained by measuring the total sum of neuronal activity levels in the epidermis of the brain.

As the method for measuring the state of the brain, there are the EEG (electroencephalogram) test, which measures and examines the brain waves received from electrodes by attaching pads with electrodes to the scalp, the CT scan which examines the brain by taking tomography from various angles by using radiation or ultrasound, the MRI scan which images the brain by magnetic resonance, and the like Various concepts are known in the field of neural stimulation of brain structures, and brain stimulation which stimulates the brain to achieve the predetermined purpose is largely classified into invasive brain stimulation and non-invasive brain stimulation.

The invasive brain stimulation is a method in which electrodes are inserted into the brain through surgery and electrical signals are applied, and the non-invasive brain stimulation is a method in which the predetermined effect is achieved by stimulating the brain without inserting the electrodes inside the skull.

Specific brain stimulation includes deep electric stimulation, transcranial magnetic stimulation (TMS), transcranial electric stimulation (TES), transcranial direct current stimulation (tDCS), and transcranial random noise stimulation (tRNS).

Among these brain stimulations, the brain electric stimulation technology by using the transcranial direct current stimulation (tDCS) is one of the relatively simple non-invasive brain stimulations that is known to be able to improve cognitive abilities or to be effective in treating various cranial nerve diseases such as depression, attention deficit hyperactivity disorder (ADHD), epilepsy, dementia, and sleep disorders, and thus, the brain stimulations are actively studied.

In the method for stimulating the brain by using the transcranial direct current stimulation (tDCS) device, the anode and the cathode are connected to the transcranial direct current stimulation (tDCS) device that generates the direct current, and when the current is injected into the anode, the current passes through the cerebrum and comes back into the cathode.

In this case, the current flows from the anode to the cathode to stimulate the cerebrum, and it may be necessary to change the direction of the electric stimulation according to the treatment method.

On the other hand, in the transcranial direct current stimulation of the related art, since a user directly selects the position to be attached and attaches the electrode to the selected position, there is a problem in that it is not possible to accurately know whether the position of the electrode selected by the user is a position capable of accurately stimulating a target point of the brain, that is, a point to be applied with the electrical stimulation.

In addition, even if the position selected by the user is a position in which the target point of the brain is accurately stimulated, there is a problem in that it is difficult to accurately attach the electrode to the position selected by the user and, particularly, it is very difficult to repeatedly attach the electrode to the same position in order to repeatedly apply the same stimulation.

Related Art—Korean Patent Registration No. 10-1758903 (2017 Jul. 11).

SUMMARY OF THE INVENTION

The present invention is to provide a method, server, and computer program for designing a customized headgear for transcranial direct current stimulation, capable of causing the electrode to be accurately attached to the optimal stimulation position and causing the electrical stimulation to be accurately applied to the target point in the brain of the subject by determining the optimal stimulation position combination for applying the electrical stimulation to the preset target point in the brain of the subject by using a result of electrical stimulation simulation using the plurality of stimulation positions according to the preset guide system (for example, 10-20 system) and generating the customized headgear mask for the subject in consideration of the optimal stimulation position included in the determined optimal stimulation position combination.

Effects of the present invention are not limited to the effects mentioned above, and other effects not mentioned will be clearly understood from the following description by those skilled in the related art.

According to an embodiment of the present invention for solving the above-described problems, there is provided a method for designing a customized headgear for transcranial direct current stimulation performed by a computing device and applying electrical stimulation to a preset target point in a brain of a subject, the method including: acquiring a head image of the subject; generating a headgear mask by using the acquired head image; generating a stimulator mask by using an optimal stimulation position combination for applying the electrical stimulation to the preset target point; and generating a customized headgear mask for the subject by performing a subtraction operation between the generated headgear mask and the generated stimulator mask.

In various embodiments, the generating the headgear mask may include: generating the head mask for the subject by using the acquired head image; and generating the headgear mask by performing image processing on the generated head mask and performing a subtraction operation between the image-processed head mask and the generated head mask.

In various embodiments, the generating the headgear mask may include setting the plurality of reference points on the generated headgear mask, and removing at least the partial area of the generated headgear mask by using the set plurality of reference points.

In various embodiments, the plurality of reference points may include four reference points corresponding to a nasion, an inion, a left pre-auricular, and a right pre-auricular of the subject, and the removing at least the partial area of the generated headgear mask may include segmenting the generated headgear mask into an upper area and a lower area based on a plane including the four reference points and removing the segmented lower area from the generated headgear mask.

In various embodiments, the plurality of reference points may include two reference points corresponding to a left pre-auricular and a right pre-auricular, the removing at least the partial area of the generated headgear mask may include generating two holes by removing at least a partial area adjacent to the two reference points, and wherein a chin strap for fixing a customized headgear manufactured using the generated customized headgear mask and a chin of the subject wearing the customized headgear is inserted into the generated two holes.

In various embodiments, the generating the headgear mask may include generating one or more holes by removing at least the partial area of the generated headgear mask, and wherein a line of an electrode attached to a head of the subject in order to apply the electrical stimulation to the preset target point is inserted into the generated holes and the inserted line of the electrode is exposed from an inside to an outside of the customized headgear manufactured by using the generated customized headgear mask through the generated holes.

In various embodiments, the generating the stimulator mask may include: simulating electrical stimulation for the brain of the subject by using a plurality of stimulation positions according to a preset guide system; determining the optimal stimulation position combination by using a simulation result of the electrical stimulation; and generating the stimulator mask based on a plurality of the optimal stimulation positions included in the determined optimal stimulation position combination.

In various embodiments, the determining the optimal stimulation position combination may include determining a plurality of the optimal stimulation position combinations for applying the electrical stimulation to the plurality of target points when there are a plurality of the preset target points, and the generating the stimulator masks corresponding to the plurality of optimal stimulation positions may include generating a plurality of the stimulator masks corresponding to the determined plurality of optimal stimulation position combinations and generating one stimulator mask by combining the generated plurality of stimulator masks.

In various embodiments, the determining the optimal stimulation position combination may include: setting the maximum number of stimulation positions to which the electrical stimulation to the preset target point is applied; and correcting the determined optimal stimulation position combination by comparing the number of optimal stimulation positions included in the determined optimal stimulation position combination with the set maximum number of stimulation positions, and the generating the stimulator masks corresponding to each of the plurality of optimal stimulation positions may include generating the stimulator masks corresponding to each of the plurality of optimal stimulation positions included in the corrected optimal stimulation position combination.

In various embodiments, the method may further include: converting the generated customized headgear mask into a three-dimensional polygonal grid structure; and manufacturing the customized headgear for the subject by three-dimensionally printing the customized headgear mask converted into the three-dimensional polygonal grid structure.

According to another embodiment of the present invention for solving the above-described problems, there is provided a server for designing a customized headgear for transcranial direct current stimulation, the server including: a processor; a network interface; a memory; and a computer program loaded on the memory and executed by the processor, wherein the computer program includes: an instruction for acquiring a head image of a subject; an instruction for generating a headgear mask by using the acquired head image; an instruction for generating a stimulator mask by using an optimal stimulation position combination for applying electrical stimulation to a preset target point in a brain of the subject; and an instruction for generating a customized headgear mask for the subject by performing a subtraction operation between the generated headgear mask and the generated stimulator mask.

According to still another embodiment of the present invention for solving the above-described problems, there is provided a computer program recorded on a computer-readable recording medium, combined with a computing device, the computer program causing the computing device to execute: acquiring a head image of a subject; generating a headgear mask by using the acquired head image; generating a stimulator mask by using an optimal stimulation position combination for applying electrical stimulation to a preset target point in a brain of the subject; and generating a customized headgear mask for the subject by performing a subtraction operation between the generated headgear mask and the generated stimulator mask.

Other specific details of the present invention are included in the detailed description and the drawings.

According to various embodiments of the present invention, there is an advantage in that, the electrode can be accurately attached to the optimal stimulation position, and the electrical stimulation can be accurately applied to the target point in the brain of the subject by determining the optimal stimulation position combination for applying the electrical stimulation to the preset target point in the brain of the subject by using a result of electrical stimulation simulation using the plurality of stimulation positions according to the preset guide system (for example, 10-20 system) and generating the customized headgear mask for the subject in consideration of the optimal stimulation position included in the determined optimal stimulation position combination.

Effects of the present invention are not limited to the effects mentioned above, and other effects not mentioned will be clearly understood from the following description by those skilled in the related art.

BRIEF DESCRIPTION OF THE DRAWINGS

FIG. 3 is a flowchart of a method for determining an optimal stimulation position combination by using a preset guide system in various embodiments.

FIG. 4 is a flowchart illustrating a method for simulating electrical stimulation using a three-dimensional brain map in various embodiments.

FIG. 5 is an exemplary diagram illustrating an MRI image of a brain of a subject and a result of segmentation thereof, according to various embodiments of the present invention;

FIGS. 17 and 18 are exemplary diagrams illustrating a third UI provided by the customized headgear design server for transcranial direct current stimulation in various embodiments.

DETAILED DESCRIPTION OF THE PREFERRED EMBODIMENTS

Figure 1:
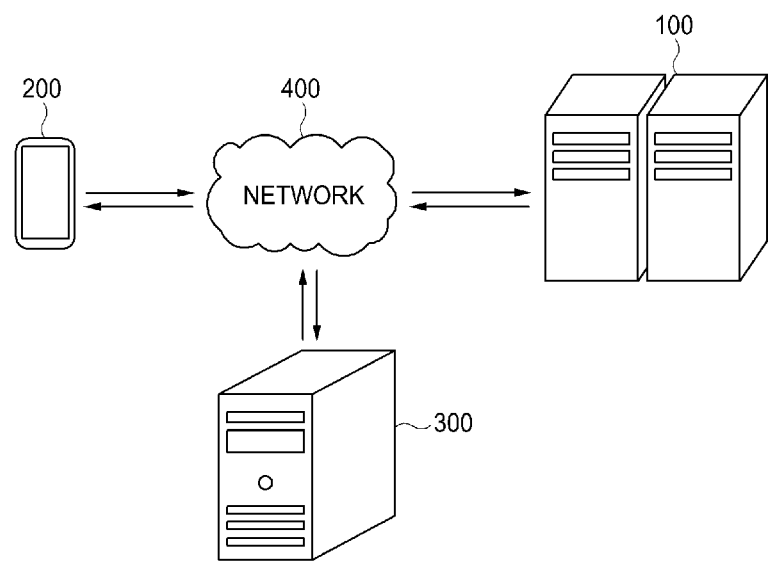
FIG. 1 is a diagram illustrating a customized headgear design system for transcranial direct current stimulation according to an embodiment of the present invention.

Advantages and features of the present invention and methods of achieving the advantages and features will become apparent with reference to embodiments described below in detail in association with the accompanying drawings. However, the present invention is not limited to the embodiments disclosed below, but the present invention may be implemented in various different forms, only the embodiments allow the disclosure of the present invention to be complete, the present invention is provided in order for the ordinarily skilled in the related art to which the present invention belongs to fully understand the scope of the present invention, and the present invention is only defined by the scope of the claims.

The terms used herein are for the purpose of describing the embodiments and is not intended to limit the present invention. In this specification, a singular form also includes a plural form unless a phrase specifically states otherwise. As used in this specification, "comprises" and/or "comprising" does not exclude the presence or addition of one or more other components in addition to the stated components. Throughout the specification, the same or similar reference numerals refer to the same or similar elements, and "and/or" includes each and all combination of one or more of the stated elements. Although "first", "second", and the like are used to describe various elements, of course, these elements are not limited by these terms. These terms are only used to distinguish one component from other components. Accordingly, it goes without saying that a first component mentioned below may be a second component within the spirit of the present invention.

Unless otherwise defined, all terms (including technical and scientific terms) used herein may be used with the meaning commonly understood by the ordinarily skilled in the related art to which the present invention belongs. In addition, terms defined in a commonly used dictionary are not to be interpreted ideally or excessively unless specifically defined explicitly.

As used in this specification, the term "unit" or "module" refers to a software component or a hardware component such as FPGA or ASIC, and the "unit" or "module" performs a certain role. However, the "unit" or "module" is not intended to be limited to software or hardware. The "unit" or "module" may be configured to reside on an addressable storage medium or may be configured to reproduce one or more processors. Accordingly, as an example, the "unit" or "module" includes components such as software components, object-oriented software components, class components and task components, processes, functions, attributes, procedures, subroutines, segments of program codes, drivers, firmware, microcode, circuits, data, database, data structures, tables, arrays, and variables. The components and functions provided within the "unit" or "module" may be combined into a smaller number of components and "units" or "modules" or may be further separated in to additional components and "units" or "modules".

Spatially relative terms "below", "beneath", "lower", "above", "upper", and the like may be used to easily describe the relationship between a certain component and other components. Spatially relative terms should be understood as terms that include different directions of components during use or operation in addition to the directions illustrated in the drawings. For example, in a case where a component illustrated in the drawings is turned over, a component described as "below" or "beneath" of the other component may be placed "above" of the other component. Accordingly, the exemplary term "below" may include both directions below and above. Components may also be oriented in other orientations, and thus, spatially relative terms may be interpreted according to orientation.

In this specification, a computer denotes all types of hardware devices including at least one processor and may be understood as collectively including software configurations operating in a corresponding hardware device according to embodiments. For example, a computer may be understood as meaning including all of a smartphone, a tablet PC, a desktop, a notebook, and a user client and an application running in each device, but the present invention is not limited thereto.

Hereinafter, an embodiment of the present invention will be described in detail with reference to the accompanying drawings.

Each step described in this specification is described as being performed by a computer, but the object of each step is not limited thereto, and at least a portion of each step may be performed in different devices according to embodiments.

FIG. 1 is a diagram illustrating a customized headgear design system for transcranial direct current stimulation according to an embodiment of the present invention.

Referring to FIG. 1, the customized headgear design system for transcranial direct current stimulation according to the embodiment of the present invention may include a customized headgear design server 100 for transcranial direct current stimulation (hereinafter, a "server 100"), a user terminal 200, and an external server 300.

Herein, the customized headgear design system for transcranial direct current stimulation illustrated in FIG. 1 may be according to the embodiment, and the components may not be limited to the embodiment illustrated in FIG. 1 and may be added, changed, or deleted.

In the embodiment, the server 100 may determine an optimal stimulation position combination for applying the electrical stimulation to a preset target point of the brain of a subject (for example, a patient) according to transcranial direct current stimulation (tDCS) and may design the customized headgear for the subject so that electrical stimulation may be applied by accurately attaching electrodes to each of the plurality of optimal stimulation positions included in the determined optimal stimulation position combination.

In various embodiments, the server 100 may simulate the electrical stimulation for the brain of the subject based on the preset guide system that defines the plurality of stimulation positions with respect to the brain of the subject in order to perform a transcranial direct current stimulation method, using the simulation result, may determine the optimal stimulation position combination for accurately applying the electrical stimulation to the specific target point, and may provide information on the determined optimal stimulation position combination.

Herein, the information on the optimal stimulation position combination determined and provided according to the above-described method not only may include information on an electrode attachment position for accurately applying the electrical stimulation to the preset target point in the brain of the subject, but also may include information (that is, a current value, a current application time, or the like) on how much the current value and how long the current (that is, the current value, current application time, or the like) is to be applied through the electrode attached to the stimulation position, but the present invention is not limited thereto.

In addition, the server 100 may generate the customized headgear mask for the subject by using the head image of the subject and the optimal stimulation position combination determined according to the above-described method and may generate the customized headgear by using the optimal stimulation position combination through three-dimensional printing.

In various embodiments, the server 100 may be connected to the user terminal 200 through the network 400 and may provide a service of determining the optimal stimulation position combination by using the preset guide system, a service providing information on the optimal stimulation position combination determined by using the service, and a service of designing the customized headgear by using the determined optimal stimulation position combination. In this case, the service provided by the server 100 may be implemented in the form of web or application, but the present invention is not limited thereto.

Figure 12:
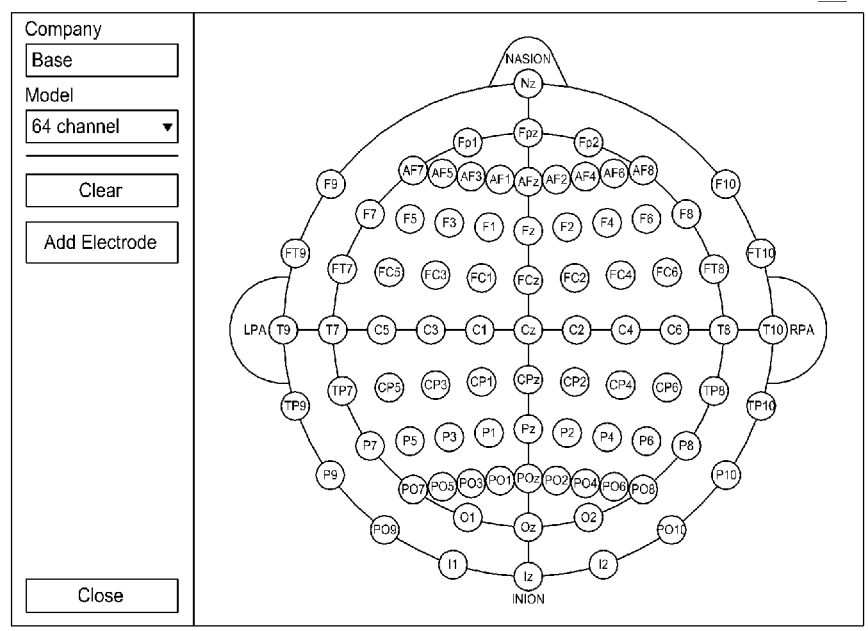
FIG. 12 is an exemplary diagram illustrating a first user interface (UI) provided by a customized headgear design server for transcranial direct current stimulation in various embodiments.
Figure 14:
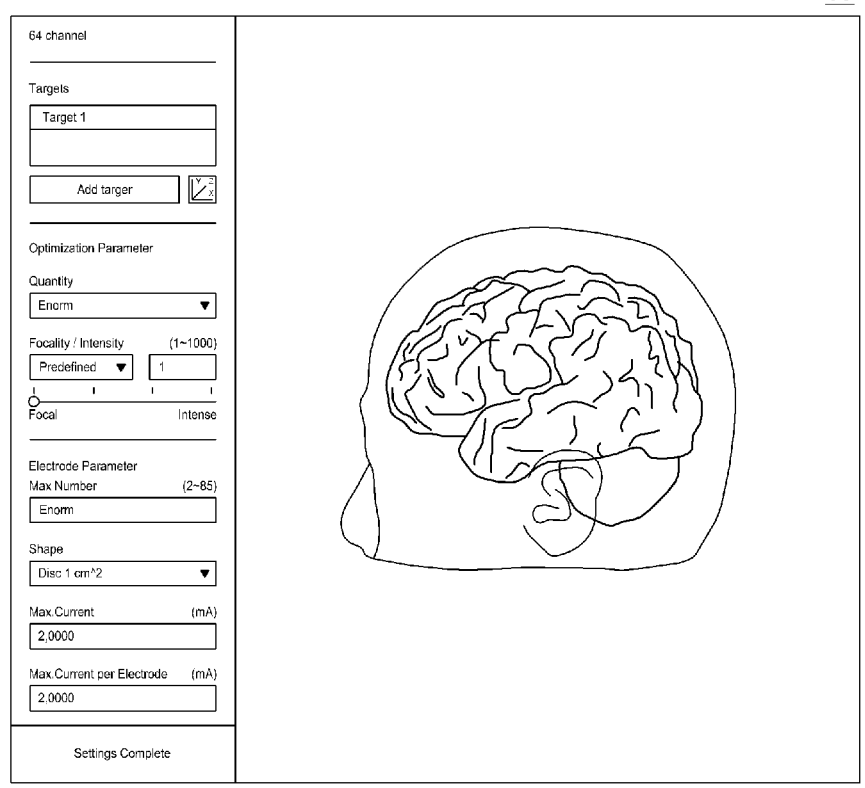
FIGS. 14 and 15 are exemplary diagrams illustrating a second UI provided by the customized headgear design server for transcranial direct current stimulation in various embodiments.
Figure 17:
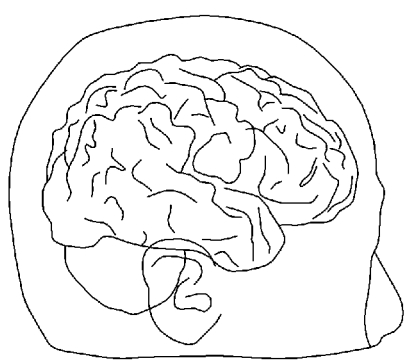

Herein, the user terminal 200 may include an operating system capable of driving the application in order to execute the application-type service provided by the server 100 and may be a smartphone including a display in a predetermined area in order to output an UI (for example, the first UI 50 of FIG. 12, the second UI 60 of FIGS. 14 and 15, and the third UI 70 of FIGS. 17 and 18) provided by the server 100, but the present invention is not limited thereto. The user terminal 200 is a wireless communication device that guarantees portability and mobility and includes all types of handheld-based wireless communication device such as a navigation, a personal communication system (PCS), a global system for mobile communications (GSM), a personal digital cellular (PDC), a personal handy phone system (PHS), a personal digital assistant (PDA), an international mobile telecommunication (IMT)-2000, a code division multiple access (CDMA)-2000, a W-code division multiple access (W-CDMA), a wireless broadband internet (Wibro) terminal, a smartphone, a smart pad (Smartpad), and a tablet PC.

In addition, herein, the network 400 may denote a connection structure capable of exchanging information between respective nodes such as a plurality of terminals and servers. For example, the network 400 may include a local area network (LAN), a wide area network (WAN), the Internet (WWW: World Wide Web), a wired/wireless data communication network, a telephone network, a wired/wireless television communication network, or the like.

In addition, herein, the wireless data communication network may include 3G, 4G, 5G, 3GPP (Third Generation Partnership Project), 5GPP (Fifth Generation Partnership Project), LTE (Long Term Evolution), WIMAX (World Interoperability for Microwave Access), Wi-Fi, the Internet, LAN (Local Area Network), Wireless LAN (Wireless Local Area Network), WAN (Wide Area Network), PAN (Personal Area Network), RF (Radio Frequency), Bluetooth network, NFC (Near-Field Communication) networks, satellite broadcasting networks, analog broadcasting networks, DMB (Digital Multimedia Broadcasting) networks, or the like, but the present invention is not limited thereto.

In one embodiment, the external server 300 may be connected to the server 100 through the network 400, the server 100 may provide information and data (for example, pre-operation information, calculation model for simulation, or the like) necessary to provide the method for determining the optimal stimulation position combination by using the preset guide system and the method for designing the customized headgear for transcranial direct current stimulation, and may store and manage various types of information and data (for example, a customized headgear mask) generated by the server 100 performing the above-described method.

In various embodiments, the external server 300 may be the storage server separately provided outside the server 100, but the present invention is not limited thereto. Hereinafter, the hardware configuration of the server 100 performing the customized headgear designing method for transcranial direct current stimulation will be described with reference to FIG. 2.

Figure 2:
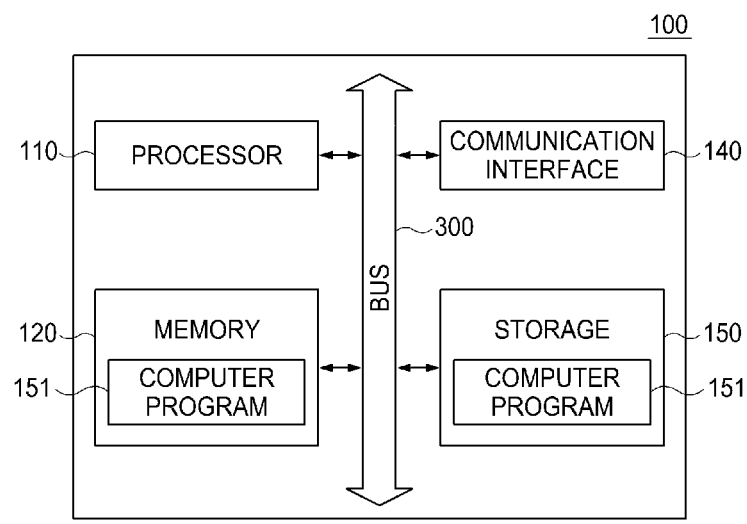
FIG. 2 is a hardware configuration diagram of a customized headgear design server for transcranial direct current stimulation according to another embodiment of the present invention.

FIG. 2 is a hardware configuration diagram of a customized headgear design server for transcranial direct current stimulation according to another embodiment of the present invention.

Referring to FIG. 2, in various embodiments, the server 100 may include one or more processors 110, a memory 120 on which a computer program 151 executed by the processor 110 is loaded, a bus 130, a communication interface 140, and a storage 150 for storing the computer program 151. Herein, FIG. 2 illustrates only the components related to the embodiment of the present invention. Accordingly, one of ordinary skill in the related art to which the present invention pertains may know that other general-purpose components in addition to the components illustrated in FIG. 2 may be further included.

The processor 110 controls the overall operation of each component of the server 100. The processor 110 may be configured to include a central processing unit (CPU), a micro processor unit (MPU), a micro controller unit (MCU), a graphic processing unit (GPU), or an arbitrary type of processor well known in the related art.

In addition, the processor 110 may perform the operation for at least one application or program for executing the method according to the embodiments of the present invention, and the server 100 may include one or more processors.

In various embodiments, the processor 110 may further include the random access memory (RAM) and the read-only memory (ROM, not illustrated) that temporarily and/or permanently store the signal (or data) processed inside the processor 110. In addition, the processor 110 may be implemented in the form of the system on chip (SoC) including at least one of a graphic processing unit, a RAM, and a ROM.

The memory 120 stores various data, commands and/or information. The memory 120 may load the computer program 151 from the storage 150 to execute methods/operation according to various embodiments of the present invention. When the computer program 151 is loaded on the memory 120, the processor 110 may perform the method/operation by executing one or more instructions constituting the computer program 151. The memory 120 may be implemented as a volatile memory such as a RAM, but the technical scope of the present invention is not limited thereto.

A bus 130 provides communication functions between components of the server 100. The bus 130 may be implemented as various types of buses such as an address bus, a data bus, and a control bus.

The communication interface 140 supports wired/wireless Internet communication of the server 100. In addition, the communication interface 140 may support various communication methods other than Internet communication. To this end, the communication interface 140 may be configured to include the communication module well known in the related art. In some embodiments, the communication interface 140 may be omitted.

The storage 150 may non-temporarily store the computer program 151. When performing the process of designing the customized headgear for transcranial direct current stimulation through the server 100, the storage 150 may store various types of information necessary to provide the process of designing the customized headgear for transcranial direct current stimulation.

The storage 150 may be configured to include a non-volatile memory such as a read only memory (ROM), an erasable programmable ROM (EPROM), an electrically erasable programmable ROM (EEPROM), or a flash memory, a hard disk, a detachable disk, or any type of a computer-readable recording medium that is well known in the technical field to which the present invention pertains.

The computer program 151, when loaded on the memory 120, may include one or more instructions that cause the processor 110 to perform methods/operation according to various embodiments of the present invention. That is, the processor 110 may perform the method/operation according to various embodiments of the present invention by executing the one or more instructions.

In the embodiment, the computer program 151 may include one or more instructions causing a method for designing a customized headgear for transcranial direct current stimulation to be performed, wherein the method includes: acquiring a head image of a subject; generating a headgear mask by using the acquired head image; generating a stimulator mask by using an optimal stimulation position combination for applying the electrical stimulation to the preset target point; and generating a customized headgear mask for the subject by performing a subtraction operation between the generated headgear mask and the generated stimulator mask.

In addition, the computer program 151 may include one or more instructions for performing the method for determining the optimal stimulation position combination by using the preset guide system, which includes: simulating the electrical stimulation for the brain of the subject by using the plurality of stimulation positions according to the preset guide system; and determining the optimal stimulation position combination for applying the electrical stimulation to the preset target point in the brain of the subject by using a result of simulating the electrical stimulation.

In addition, the computer program 151 may include one or more instruction to perform the electrical stimulation simulation method for determining the optimal stimulation position combination including filtering the stimulation positions corresponding to the preset conditions among the plurality of stimulation positions according to the preset guide system and simulating the electrical stimulation for the brain of the subject by using the remaining stimulation positions except for the filtered stimulation positions among the plurality of stimulation positions.

The steps of the method or algorithm to be described in relation to the embodiment of the present invention may be implemented directly in hardware, implemented as a software module executed by hardware, or implemented by a combination thereof. A software module may reside in a random access memory (RAM), a read only memory (ROM), an erasable programmable ROM (EPROM), an electrically erasable programmable ROM (EEPROM), a flash memory, a hard disk, a detachable disk, a CD-ROM, or any type of a computer-readable recording medium that is well known in the technical field to which the present invention pertains.

The components of the present invention may be implemented as a program (or application) to be executed in combination with a computer, which is hardware, and stored in the medium. The components of the present invention may be implemented as software programming or software components, and similarly, the embodiments may be implemented in programming or scripting languages such as C++, Java, assembler, or the like including various algorithms implemented as data structures, processes, routines, or combinations of other programming structures. Functional aspects may be implemented in an algorithm running on one or more processors. Hereinafter, the method for determining the optimal stimulation position combination by using the preset guide system performed by the server 100 and the method for designing the customized headgear for transcranial direct current stimulation will be described with reference to FIGS. 3 to 20.

FIG. 3 is a flowchart of the method for determining the optimal stimulation position combination by using the preset guide system in various embodiments.

Referring to FIG. 3, in step S110, the server 100 may simulate the electrical stimulation for the brain of the subject by using the plurality of stimulation positions according to the preset guide system.

Figure 8:
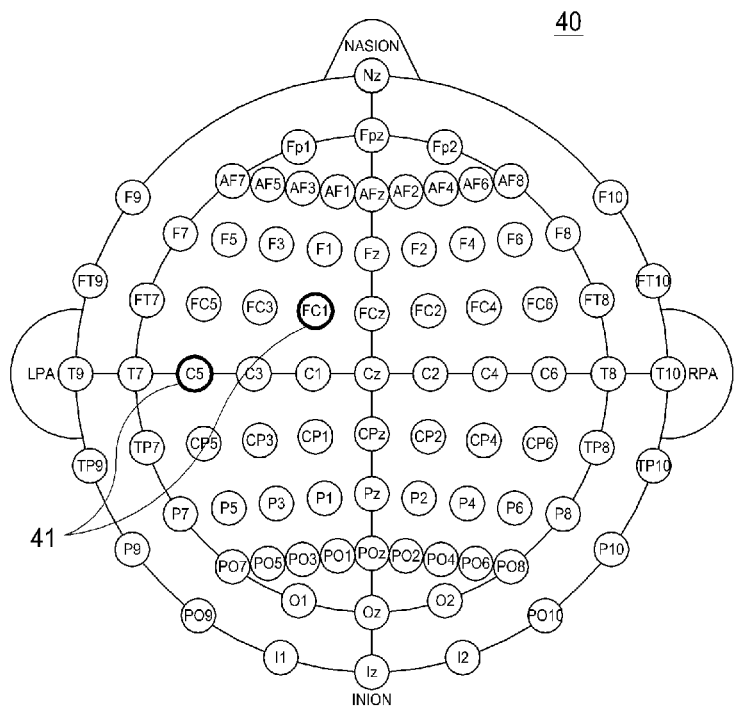
FIG. 8 is an exemplary diagram illustrating a form in which an optimal stimulation position combination is determined among a plurality of stimulation positions according to a 10-20 system according to various embodiments.

Herein, the preset guide system may denote a system that defines a plurality of stimulation positions for the brain of the subject in advance in order to perform guiding with transcranial direct current stimulation and, accordingly, guides the electrode attachment position to apply the electrical stimulation to the target point of the brain. For example, as illustrated in FIG. 8, the preset guide system may be an EEG measurement 10-20 system 40 according to the International 10-20 System Standard Electrode Attachment Method, and the plurality of stimulation positions may denote positions where the plurality of brainwave measurement channels (19, 24, 68, 128, or 256 caps or individual electrodes) are attached to the head of the subject according to the 10-20 system, but the present invention is not limited thereto.

In various embodiments, the server 100 may generate the three-dimensional brain map corresponding to the brain of the subject and simulate the electrical stimulation using the plurality of stimulation positions by using the generated three-dimensional brain map. Hereinafter, it will be described with reference to FIGS. 4 to 7.

FIG. 4 is a flowchart illustrating the method for simulating electrical stimulation using a three-dimensional brain map in various embodiments.

Referring to FIG. 4, in step S210, the server 100 may acquire the magnetic resonance imaging (MRI) image (for example, 10 of FIG. 5A) of the brain of the subject.

Herein, the MRI image of the brain of the subject may denote the MRI image obtained by imaging the head including the brain of the subject. That is, the MRI image of the brain of the subject may include not only the brain of the subject but also the skull and scalp of the subject. For example, the server 100 may be connected to the computer that is a workstation connected to an MRI image acquisition device and may directly acquire the brain MRI image of the subject through the computer from the MRI image acquisition device. However, the present invention is not limited thereto.

In step S220, the server 100 may segment the MRI image acquired in step S210 into the plurality of areas (for example, 11 in FIG. 5B).

In various embodiments, the server 100 may generate the plurality of areas by analyzing the acquired MRI image and segmenting the MRI image into brain areas. For example, the server 100 may segment the MRI image into the white matter area, the gray matter area, the cerebrospinal fluid area, the skull area, and the scalp area of the brain, but the present invention is not limited thereto.

In various embodiments, the server 100 may segment the MRI image into the plurality of areas by analyzing the MRI image of the pre-trained AI model.

Herein, the pre-trained AI model includes one or more batch normalization layers, activation layers, and convolution layers, and the pre-trained AI model may be an AI model learned according to a machine learning-based learning method by setting an MRI image segmented into a plurality of areas according to areas of the brain as learned data (for example, a model learned by using machine learning, particularly, a model learned by using deep learning).

In addition, the pre-trained AI model may be configured to include a horizontal pipeline configured with a plurality of blocks for extracting high-level properties from low-level properties of the MRI image and a vertical pipeline for performing the segmentation by collecting the properties extracted from the horizontal pipelines so as to perform the segmentation on the MRI image with poor image quality, but the present invention is not limited thereto.

In various embodiments, the server 100 may perform a post-process on the MRI image segmented into the plurality of areas according to the above-described method.

Figure 6:
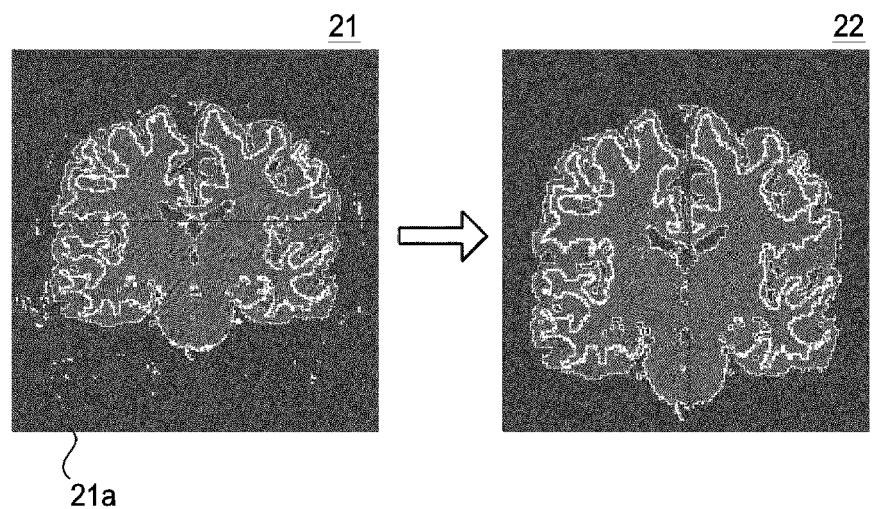
FIG. 6 is a diagram illustrating a process of removing noise from the MRI image segmented into a plurality of areas by performing noise cancellation based on a connected component, according to various embodiments.

First, referring to FIG. 6, the server 100 may perform connected component-based noise rejection on the MRI image segmented into the plurality of areas.

Herein, the connected component-based noise rejection may be utilized in the process of improving the results of MRI image segmentation performed by using the convolutional neural network (CNN). For example, the server 100 may generate the MRI image 22 from which noise is removed by removing the remaining components 21a except for the connection component, which is the largest chunk, in the MRI image 21 segmented into the plurality of areas as illustrated in FIG. 6.

Herein, various techniques are known in relation to the method for performing the connection component-based the noise rejection, and these various known techniques may be selectively applied depending on the situation, and thus, in this specification, the method for the connection component performed by the server 100 is not specifically disclosed.

Figure 7:
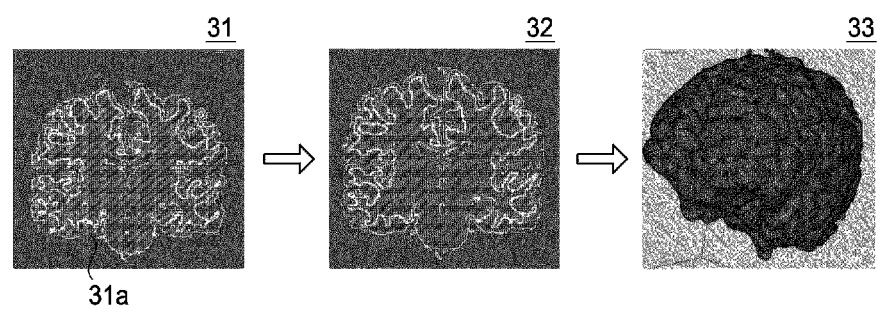
FIG. 7 is a diagram illustrating a process of performing hole rejection on the MRI image segmented into the plurality of areas and generating a three-dimensional brain image by using this MRI image, according to various embodiments.

Thereafter, referring to FIG. 7 the server 100 may perform hole rejection on the MRI image segmented into the plurality of areas. Herein, hole rejection may be utilized to reject holes, which is one of errors in convolutional neural network-based segmentation. For example, the server 100 may generate the MRI image 32 from which the holes have been removed by removing at least a portion of holes 31A included in the MRI image 31 segmented into the plurality of areas.

Herein, with respect to the method for performing the hole rejection, various techniques are known as in the method for performing the connection component-based noise rejection, and these various known techniques can be selectively applied depending on the situation. Therefore, in the present specification, the method of causing the server 100 to perform the hole rejection is not specifically disclosed.

In step S230, the server 100 may generate the three-dimensional brain image (for example, 33 of FIG. 7) by using the MRI image segmented into the plurality of areas (for example, the MRI image from which noise and holes are removed).

In step S240, the server 100 may generate a three-dimensional brain map configured with a plurality of grids (meshes) capable of simulating a delivery process of the electric stimulation based on the attributes of each of the plurality of areas included in the three-dimensional brain image generated through step S230. For example, the server 100 may generate the three-dimensional stereoscopic image configured with a plurality of spatial meshes (volumetric meshes) including a tetrahedron or a hexahedron or generate the three-dimensional stereoscopic image configured with a plurality of surface grids (surface meshes) including a triangle or a square, but the present invention is not limited thereto, and the type of grid constituting the three-dimensional stereoscopic image may be set differently depending on the application of simulation.

In step S250, the server 100 may simulate the electrical stimulation for the plurality of stimulation positions by using the three-dimensional brain map configured with the plurality of grids.

In various embodiments, the server 100 may generate the pre-operation information by precomputing some operation processes of the simulation in order to improve the efficiency of the simulation process such as increasing the operation speed of the simulation and may simulate the electrical stimulation for the plurality of stimulation positions by using the pre-operation information.

First, the server 100 may acquire physical property of each of the plurality of areas for simulating the flow of current according to electrical stimulation for the brain of the subject as pre-operation information.

Herein, the physical property may be electrical conductivity (for example, at least one of isotropic electrical conductivity and anisotropic electrical conductivity of each of the plurality of areas), but the present invention is not limited thereto.

In various embodiments, the server 100 may assign the electrical conductivity known through the experiment to each of the plurality of segmented areas (for example, white matter: 0.126 S/m, gray matter: 0.276 S/m, cerebrospinal fluid: 1.65 S/m, skull: 0.01 S/m, and skin: 0.465 S/m).

In addition, the server 100 may acquire the anisotropic electrical conductivity for each of the plurality of areas from the MRI image including a conduction tensor image of the brain of the subject. For example, the server 100 may acquire the anisotropic electrical conductivity according to the direction of the nerve fiber included in the diffusion tensor image in consideration that the eigenvector of the diffusion tensor image coincides with the eigenvector of the conduction tensor.

Thereafter, the server 100 may set one position among the plurality of stimulation positions as a reference stimulation position and may perform simulation while changing other remaining stimulation positions except for the reference stimulation position among the plurality of stimulation positions based on the set reference stimulation position.

For example, the server 100 may calculate the coordinate system of the preset guide system (for example, the 10-20 system) based on the head image of the subject. Thereafter, the server 100 may set the reference stimulation position among the plurality of stimulation positions and may perform the simulation by configuring the set reference stimulation position and at least one stimulation position among the remaining stimulation positions (remaining stimulation positions except for the reference stimulation positions among the plurality of stimulation positions) as one stimulation position combination.

That is, the server 100 may determine the stimulation position combination including one reference stimulation position and at least one stimulation position among other stimulation positions except for the reference stimulation position and may acquire the stimulation result by performing the simulation for each stimulation position combination.

In various embodiments, the server 100 may arbitrarily select two or more stimulation positions among the plurality of stimulation positions and may acquire stimulation results by performing the simulation on the arbitrarily selected two or more stimulation positions.

Herein, the server 100 simulates electrical stimulation by using a three-dimensional brain map configured with the plurality of grids. The server 100 may perform simulation for the plurality of electrical stimulation positions by using at least one of a finite difference method (FDM), a finite volume method (FVM), and a finite element method (FEM) that simulate by using the three-dimensional model having a grid structure, but the present invention is not limited thereto.

Thereafter, the server 100 may derive the linear relationship for each of the plurality of stimulation positions as pre-operation information for the simulation by using the simulation result generated by applying the electrical stimulation to each of the plurality of stimulation positions according to the preset guide system.

For example, the stimulation results collected by applying the electrical stimulation to each of the plurality of stimulation positions have the linear characteristic, and the server 100 may derive the linear relationship between the plurality of electrical stimulation positions by using the stimulation results collected by applying the electrical stimulation to each of the plurality of stimulation positions. For example, since the electric field and the current density due to stimulation have the linear relationship with each other, the linear relationship as illustrated in Equation 1 below may be derived.

$$E(C1_a, C2_b, C3_{-a-b}) = E(C1_a, C3_{-a}) + E(C2_b, C3_{-b}) \quad \langle \text{Equation 1} \rangle$$

Herein, E (C1a, C2b) may be the current distribution in the brain when the currents a and b are applied to C1 which is a first stimulation position and C2 which is a second stimulation position, respectively.

That is, by using the linear relationship as in Equation 1 above, the linear equation of the form Ax=E may be derived (herein, x is an amount of the current applied to the electrical stimulation position, E is an electric field value), and the desired E value, that is, the electric field value may be linearly calculated by adjusting the x value.

Herein, the x value may be an M×1 matrix (where M is the number of stimulation positions (or electrodes) used in the simulation), E may be an N×1 matrix (where N is the number of nodes included in the three-dimensional brain map), and A may be an N×M matrix (herein, each column of the N×M matrix is a pre-operation result). That is, the server 100 may calculate the matrix A as a linear relationship for each of the plurality of stimulation positions, that is, pre-operation information.

In various embodiments, when the number of the plurality of stimulation positions is n, the server 100 may derive the linear relationship for each of the plurality of stimulation positions only by n−1 simulations. For example, when the simulation is performed on the sum of three stimulation positions (for example, the first stimulation position, the second stimulation position, and the third stimulation position), the linear relationship between the second and third stimulation positions may be deduced through the simulation results for the first and second stimulation positions and the simulation results for the first and third stimulation positions, and thus, the linear relationship for each of the three electrical positions may be derived through only the two times of simulation for the three stimulation positions.

In various embodiments, the server 100 may filter the stimulation position corresponding to the preset condition among the plurality of stimulation positions and may simulate the electrical stimulation for the brain of the subject by using the remaining stimulation positions except for the filtered stimulation positions among the plurality of stimulation positions in the brain of the subject.

Hereinafter, it will be described with reference to FIGS. 9 to 12.

Figure 9:
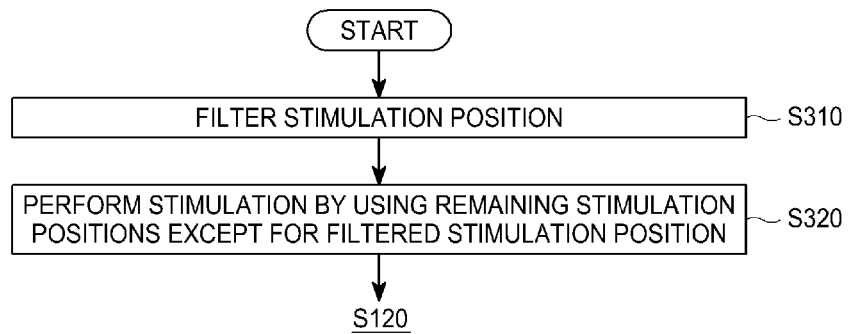
FIG. 9 is a flowchart illustrating a method for simulating electrical stimulation by filtering the stimulation position in various embodiments.

FIG. 9 is a flowchart illustrating a method for simulating electrical stimulation by filtering the stimulation position in various embodiments.

Referring to FIG. 9, in step S310, the server 100 may filter the stimulation positions corresponding to the preset conditions among the plurality of stimulation positions according to the preset guide system.

In various embodiments, the server 100 may filter at least one stimulation position by using the head image of the subject.

First, the server 100 may acquire the head image generated by imaging the head of the subject and may set one or more reference stimulation positions based on the acquired head image. For example, the server 100 may provide the first UI (for example, 50 in FIG. 12) to the user terminal 200, may output the plurality of stimulation positions according to the preset guide system through the first UI, and may set the reference stimulation position by selecting one or more of the plurality of output stimulation positions as the reference stimulation position. However, the present invention is not limited thereto, and various methods such as the method for automatically setting reference stimulation positions for calculating the plurality of stimulation positions according to the preset guide system by image analysis of the head image of the subject may be applied.

Thereafter, the server 100 may set the plurality of stimulation positions based on one or more reference stimulation positions. For example, in the case where the total number of reference stimulation positions set according to the above method is four and the four stimulation positions corresponding to the nasion, the inion, the left pre-auricular, and the right pre-auricular of each subject are Nz, Iz, LPA, and RPA, the server 100 may calculate the point where the first connection line that connects the stimulation positions Nz and Iz corresponding to the nasion and the inion and the second connection line that connects the stimulation positions LPA and RPA corresponding to the left pre-auricular and the right pre-auricular intersect as the central coordinate and may derive the coordinate system for the plurality of stimulation positions according to the 10-20 system by using the distance information on the first connection line and the second connection line based on the central coordinate. As the example, the server 100 may derive the coordinate system of the 10-20 system so as to have a position where the first connection line and the second connection line are segmented with distances of 10% or 20%, respectively, based on the central coordinates.

Thereafter, the server 100 may set the filtering target area (for example, the reference area for filtering the stimulation position) by using the plurality of stimulation positions set on the head image and may filter at least one of stimulation positions based on the set filtering target area.

Figure 10:
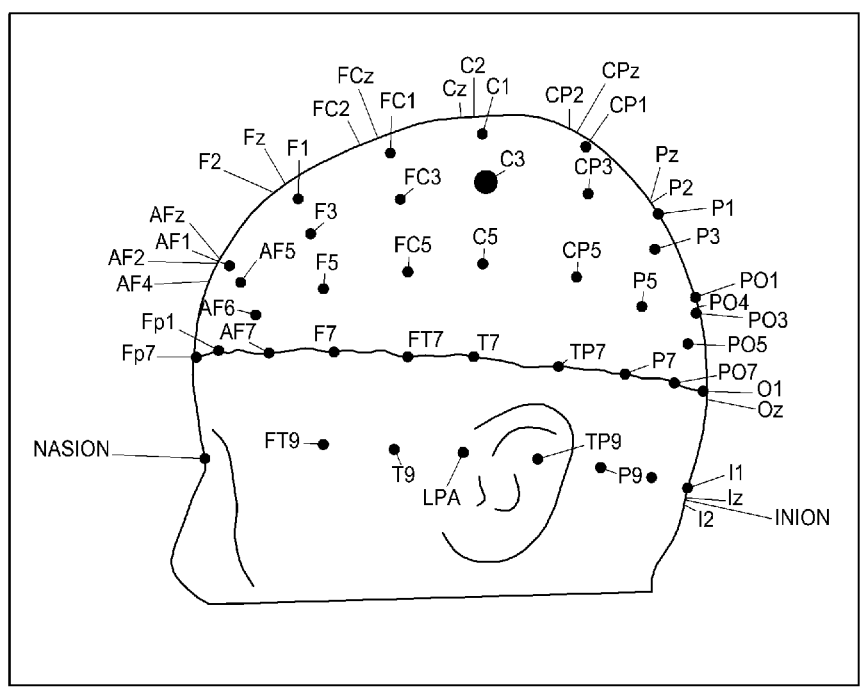
FIG. 10 is an exemplary diagram illustrating a form of filtering at least one stimulation position by setting the filtering target area in various embodiments.

In various embodiments, the server 100 may set a plane including one or more reference stimulation positions as a filtering target area and may filter at least one stimulation position positioned on the plane set as a filtering target area based on the plane set as a filtering target area. For example, as illustrated in FIG. 10, when one or more reference stimulation positions are four stimulation positions (Nz, Iz, LPA, and RPA) corresponding to the nasion, the inion, the left pre-auricular, and the right pre-auricular, the server 100 may set the plane including Nz, Iz, LPA, and RPA as the filtering target area and may filter all stimulation positions positioned on the plane including Nz, Iz, LPA, and RPA.

In various embodiments, the server 100 may filter all stimulation positions positioned below the plane based on the plane set as the filtering target area. For example, when the one or more reference stimulation positions set by the user are Fpz, T7, Oz, and T10, the server 100 may filter the stimulation positions Nz, Iz, LPA, and RPA positioned at the bottom of the plane including Fpz, T7, Oz, and T10.

That is, the stimulation position corresponding to the nasion, the inion, the left pre-auricular, and the right pre-auricular is difficult to attach the electrode due to the shape of the head or the ear, or since it is difficult to attach the electrode to the accurate position even if the electrode is attached, the stimulation positions corresponding to these positions may be filtered.

In various embodiments, the server 100 may analyze the head image to detect the area in which electrode attachment is not possible on the head of the subject, may set the area in which electrode attachment is not possible as the filtering target area, and may filter at least one stimulation position included on the filtering target area. For example, if there is the injury such as the area with the metallic substance (clip, coil, metabolic foreign body, or the like), the scalp disease, or wound in the brain of the subject, there is the problem in that it is difficult to attach electrodes to the area and apply the electrical stimulation to the area. In consideration of these points, the server 100 may detect the area where electrodes cannot be attached as described above by analyzing the head image of the subject through image analysis and may filter the stimulation positions included on the detected area.

In step S320, the server 100 may simulate the electrical stimulation for the brain of the subject by using the remaining stimulation positions except for the filtered stimulation positions among the plurality of stimulation positions. Herein, the method for simulating the electrical stimulation for the brain of the subject by using the stimulation positions except for the filtered stimulation positions may be performed by using at least one of the finite element method, the finite difference method, and the finite volume method as described above.

In various embodiments, the server 100 may segment the brain of the subject into two areas, that is, the left hemisphere area and the right hemisphere area and may perform simulations individually for each of the left hemisphere area and the right hemisphere area.

Figure 11:
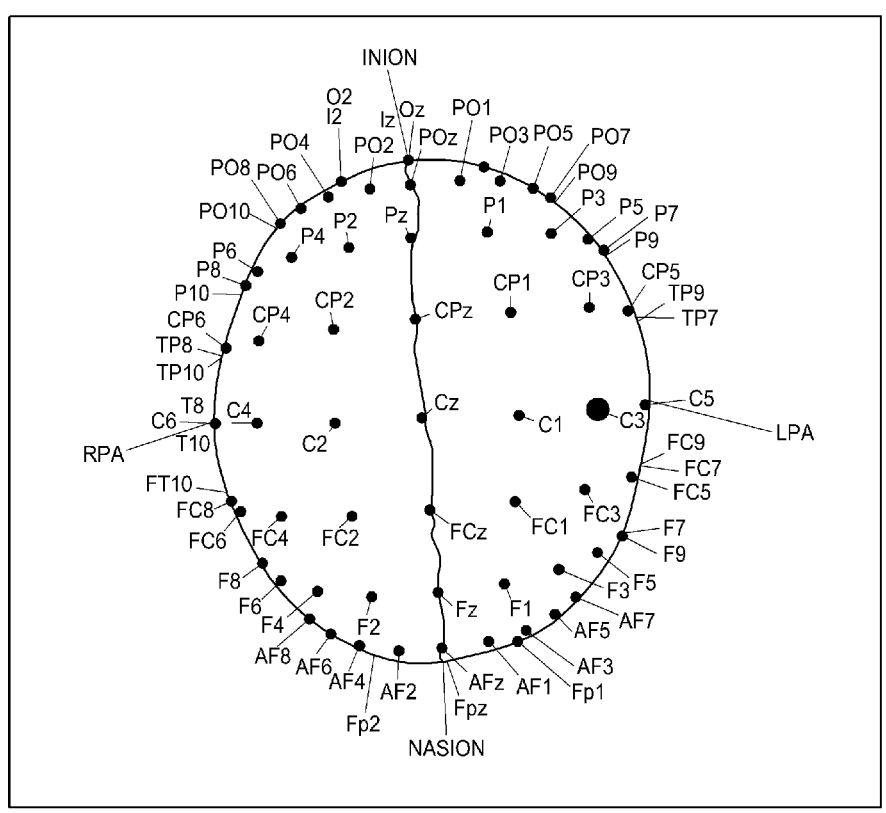
FIG. 11 is an exemplary diagram illustrating a form segmenting a brain area of the subject into a left hemisphere area and a right hemisphere area according to various embodiments.

First, as illustrated in FIG. 11, the server 100 may segment the brain area of the subject into the left hemisphere area and the right hemisphere area by using a first geodesic line connecting the first stimulation position corresponding to the nasion of the subject and the second stimulation position corresponding to the inion and a second geodesic line connecting the third stimulation position corresponding to the left pre-auricular and the fourth stimulation position corresponding to the right pre-auricular.

Thereafter, the server 100 may simulate the electrical stimulation for the left hemisphere area of the brain of the subject by selecting two or more stimulation positions positioned in the left hemisphere area among the remaining stimulation positions except for the filtered stimulation positions and may simulate the electrical stimulation for the right hemisphere area of the brain of the subject by selecting two or more stimulation positions positioned in the right hemisphere area among the remaining stimulation positions except for the filtered stimulation positions.

At this time, the server 100 may filter the stimulation positions so that currents of different polarities are not applied to the same area. For example, when any one stimulation position positioned on the left hemisphere area is selected, the server 100 may filter at least one stimulation position applied with the current having the polarity opposite to that of the current applied to any one of the above-described stimulation position (filter the stimulation position applied with a negative current when a positive current is applied to any one of the stimulation positions) among other stimulation positions positioned on the left hemisphere area, which is the same area as any one of the selected stimulation positions.

In addition, when any one stimulation position positioned on the right hemisphere area is selected, the server 100 may filter at least one stimulation position applied with the current having the polarity opposite to that of the current applied to any one of the above-described stimulation positions among other stimulation positions positioned on the right hemisphere area, which is the same area as any one of the selected stimulation positions.

That is, the server 100 may exclude the case where the anode and the cathode are positioned in the same hemisphere in order to exclude the result in which clinical verification for safety has not been made.

Unnecessary operation during the simulation may be reduced by filtering unnecessary stimulation positions in advance according to the preset conditions as described above and performing the simulation by using only the remaining stimulation positions according to the filtered result.

Referring again to FIG. 3, in step S120, the server 100 may determine the optimal stimulation position combination for applying the electrical stimulation to the preset target point in the brain of the subject by using the result of the electrical stimulation simulation performed in step S110.

In various embodiments, the server 100 may calculate the optimal stimulation position by using the linear relationship for each of the plurality of stimulation positions generated as pre-operation information.

Herein, the optimal stimulation position may denote a position to which stimulation may be applied with maximum efficiency under the given condition (for example, the area in which the electrode may be positioned, the output of the electrode, or the like) for the stimulation area suitable for the patient with the specific disease obtained by various clinical or theoretical studies.

This is similar to the method for finding the solution of the inverse problem finding the conditions for obtaining the desired result, rather than acquiring the result according to the given condition, and the numerical optimization method may be used. The above-mentioned meaning of applying stimulation with a maximum efficiency refers to stimulation conditions in which the electric field in the desired area is maximized as interpreted in terms of actual electromagnetic meaning, and the linear relationship between the specific stimulation applied to each of the plurality of stimulation positions and the electric field output according to the specific stimulation may be derived from the result of performing of the simulation of electrical stimulation in order to obtain such stimulation conditions and the pre-operation information.

In various embodiments, the server 100 can derive the linear relationship between a specific stimulation and the electric fields output by applying the specific stimulation under arbitrary stimulation conditions as illustrated in Mathematical Formula 2 below from the result of simulation of the electrical stimulation.

$$E_m(r) = \alpha B_m(r) \qquad \text{<Equation 2>}$$

Herein, E may be the electric field, r may be the coordinates of the stimulation position, m may be an arbitrary stimulation condition, a may be a ratio of an actual stimulation to a basic unit stimulation intensity, and B may be the basic unit stimulation intensity.

The electric field (E) that may be finally obtained according to Equation (2) is equal to the product of the basic unit stimulation intensity (B) of the stimulation and the ratio (a) of the actual stimulation to the basic unit stimulation intensity, and when the stimulation is applied to various stimulation combination in this method, the linear relationship between the two stimulations with different stimulation conditions may be expressed as Equation 3.

$$E_{\sum m_i}(r) = \sum_{i=1}^{n} \alpha_i B_{m_i}(r) \qquad \text{(Equation 3)}$$

Herein, mi may be the i-th stimulation condition.

Thereafter, the server 100 may derive the linear relationship between the electric fields output when the stimulation is applied according to the stimulation conditions and different stimulation condition combinations as in Equation 3.

Accordingly, since a linear system of equations for various stimulation conditions and desired stimulation intensity can be obtained, the server 100 can finally obtain the stimulation condition that the maximum stimulation can be applied to the desired stimulation position by using numerical optimization. Herein, a least square method, a weighted least square method, or an L1 norm constrained method can be applied, but the present invention is not limited thereto.

In various embodiments, the server 100 can calculate the optimal stimulation position for applying the electric stimulation to the preset target point in the brain of the subject by using the linear relationship according to Equation 3 described above. For example, since the desired result can be reversely known as the stimulation conditions including information on the target point in the brain of the subject is received as an input from the user, the server 100 can calculate the optimal stimulation position (for example, 41 of FIG. 8) to which the electric stimulation is applied and can determine the optimal stimulation position combination by configuring the calculated optimal stimulation position into as combination.

In various embodiments, the server 100 can correct the optimal stimulation position combination based on the number of maximum stimulation positions in which the electric stimulation is applied to the preset target point. Hereinafter, the description will be made with reference to FIG. 13.

Figure 13:
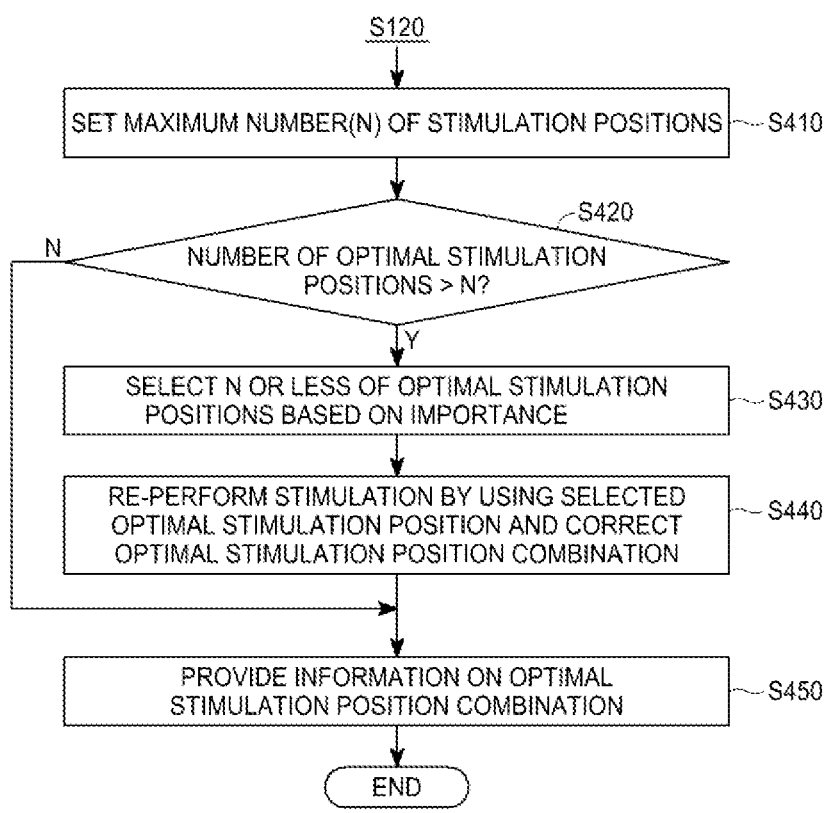
FIG. 13 is a flowchart illustrating a method for correcting the optimal stimulation position combination according to a limited number of available electrodes, according to various embodiments.

FIG. 13 is a flowchart illustrating a method for correcting the optimal stimulation position combination in accordance with a limited number of available electrodes in various embodiments.

Referring to FIG. 13, in step S410, the server 100 can set the number of maximum stimulation positions in which the electric stimulation is applied to the preset target point. For example, the server 100 can provide the second UI (60 in FIG. 14) to the user terminal 200, and can receive the number of maximum stimulation positions through the first UI 60. However, the present invention is not limited thereto.

In step S420, the server 100 can determine whether the number of the plurality of optimal stimulation positions exceeds the number of maximum stimulation positions by comparing the number of the plurality of optimal stimulation positions included in the optimal stimulation position combination determined according to the above-mentioned method (for example, steps S110 and S120 in FIG. 3) and the number of the maximum stimulation positions set in step S410.

In step S430, in a case where it is determined that the number of the plurality of optimal stimulation positions exceeds the number of the maximum stimulation positions, the server 100 can select at least one (less than or equal to the number of maximum stimulation positions) of the plurality of optimal stimulation positions among the plurality of optimal stimulation positions based on the importance of each of the plurality of optimal stimulation positions.

In various embodiments, the server 100 can set the importance for each of the plurality of optimal stimulation positions based on the positions of the plurality of optimal stimulation positions and can select at least one optimal stimulation position among the plurality of optimal stimulation positions according to the set importance. For example, in a case where the subject to be applied with the electric stimulation is a patient with diseases such as epilepsy and brain diseases, there is a region where the electric stimulation cannot be applied according to diseases such as epilepsy and brain diseases. In consideration of this, in a case where there is a region where the electric stimulation cannot be applied according to the disease of the subject as described above the server 100 can calculate the distance between the region where the electric stimulation cannot be applied and each of the plurality of optimal stimulation positions and can perform setting so as to set high importance from the optimal stimulation position having a long distance based on the calculated distance.

In various embodiments, the server 100 can set the importance for each of the plurality of optimal stimulation positions based on the current intensity applied to each of the plurality of optimal stimulation positions and can select at least one optimal stimulation position among the plurality of optimal stimulation positions according to the set importance. For example, a low current intensity applied to a specific stimulation position through an electrode denotes that the amount of stimulation applied, that is, the effect on the stimulation is small, and thus, the server 100 can perform setting so as to sequentially set higher importance according to the order of increasing the current intensity applied to each of the plurality of optimal stimulation positions.

In step S440, the server 100 can re-perform the simulation for the brain of the subject by using only at least one optimal stimulation position selected through step S430 and can correct the determined optimal stimulation position combination based on the result of the re-performed simulation.

At this time, the server 100 can perform the simulation for at least one optimal stimulation position by using only the information on the at least one optimal stimulation position in the pre-operation information, that is, by using the only remaining computation information obtained by removing the information on the filtered optimal stimulation position according to importance in the pre-operation information.

Since the pre-operation information includes information on the linear relationship for all stimulation positions, there is a problem in that differences in current intensity etc. occur between a case where the simulation is performed by using information on all the stimulation positions and a case where the simulation is performed by using only information on the selected at least one optimal stimulation position.

In addition, in a case where only the information on a specific optimal stimulation position is selectively used without removing information on the filtered optimal stimulation position according to the importance from the pre-operation information, there is a problem in that an error that cannot physically occur (for example, the total sum of input currents is 1 and the total sum of the output currents is 0.9, or the like).

In consideration of this problem, the server 100 can remove the information on the linear relationship for each of the optimal stimulation positions filtered according to importance from the pre-operation information and can re-perform the simulation by using only the information on the linear relationship between at least one optimal stimulation position selected according to the importance.

Figure 15:
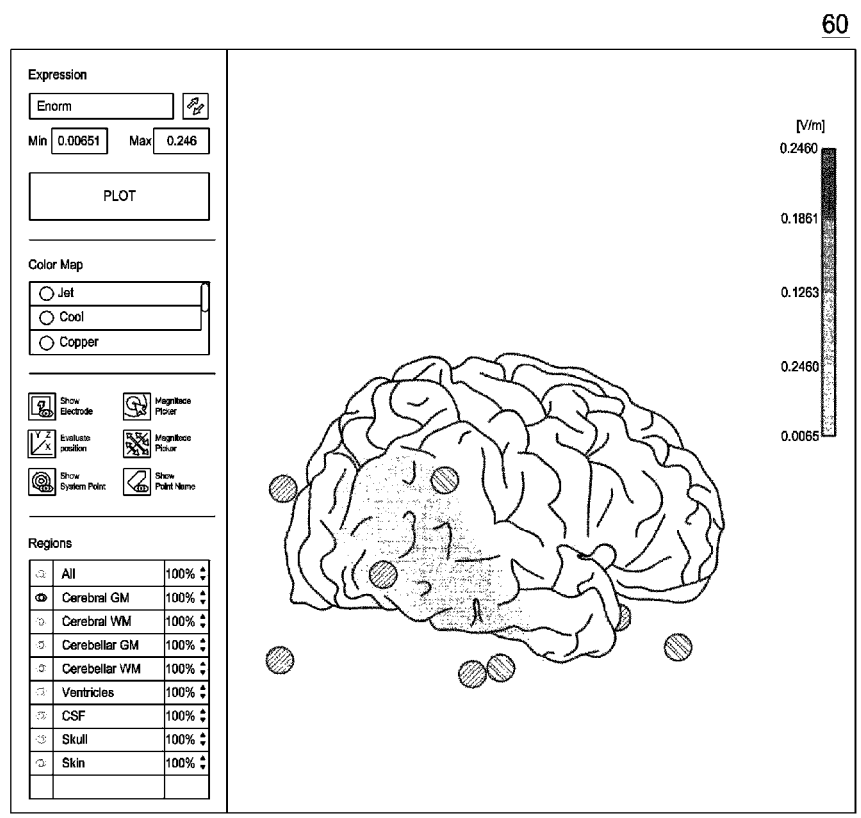

In step S450, the server 100 can determine the optimal stimulation position combination corrected through step S440 as the final optimal stimulation position combination, and can provide information on this to the user through the second UI 60 (for example, FIG. 15).

On the other hand, in a case where the number of the plurality of optimal stimulation positions is less than or equal to the number of maximum stimulation positions, at step S420, the server 100 can determine the determined optimal stimulation position combination as the final optimal stimulation position combination and can provide the information on this to the user through the second UI 60.

In various embodiments, the server 100 can standardize the current value applied to each of the plurality of optimal stimulation positions included in the optimal stimulation position combination determined according to the above-mentioned method according to the current resolution (the setting unit of the current value of a transcranial direct current stimulation (tDCS) device). Hereinafter, the description will be made with reference to FIGS. 16 to 18.

Figure 16:
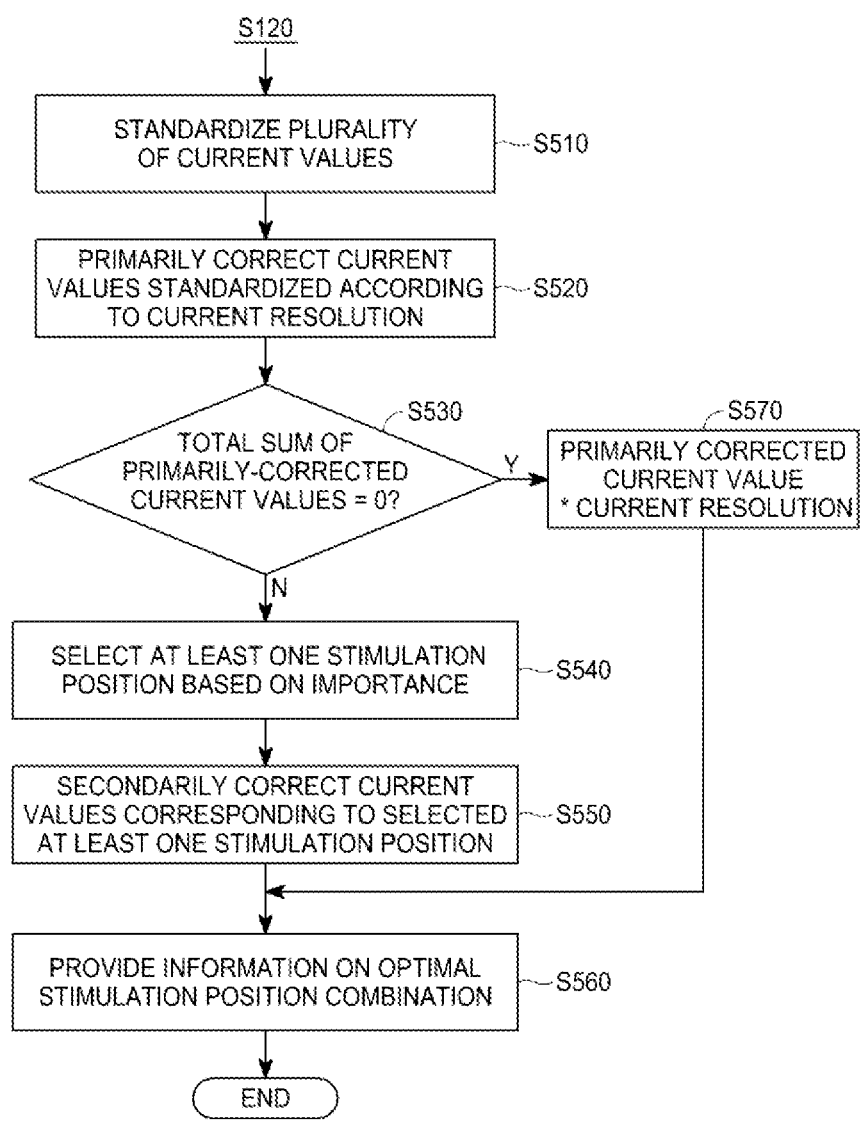
FIG. 16 is a flowchart illustrating a method for correcting a current value to be applied to the stimulation position according to a current resolution of the transcranial direct current stimulation (tDCS) device in various embodiments.

FIG. 16 is a flowchart illustrating a method for correcting the current value to be applied to the stimulation position according to the current resolution of the transcranial direct current stimulation (tDCS) device in various embodiments.

Referring to FIG. 16, in step S510, the server 100 can standardize the plurality of current values applied to each of the plurality of optimal stimulation positions included in the optimal stimulation position combination based on preset the current resolution. For example, the server 100 can provide the third UI (for example, 70 in FIG. 16) to the user terminal 200, can receive the current resolution input through the second UI 60, and can standardize the plurality of current values by dividing the plurality of current values applied to each of the plurality of optimal stimulation positions by the input the current resolution value.

In step S520, the server 100 can perform primary correction (for example, rounding up, rounding down, rounding off, or the like) on each of the plurality of current values standardized in step S510 so that each of the plurality of current values standardized in step S510 is a multiple of a preset resolution. For example, in a case where the current applied to the first optimal stimulation position is 220 mA and the preset current resolution is 200 mA, the server 100 can calculate the standardized current value of 1.1 obtained by dividing the current value applied to the first optimal stimulation position by the preset current resolution and can correct the standardized current value from 1.1 to 1 for the first optimal stimulation position by rounding off the calculated standardized current value so as to be a multiple of the preset current resolution (that is, the standardized current value has a natural number value such as 1, 2, and 3). In addition, in a case where the current applied to the second optimal stimulation position is 350 mA, the server 100 can calculate the standardized current value of 1.5 by dividing the current value applied to the second optimal stimulation position by the preset current resolution and can correct the standardized current value from 1.5 to 2 for the second optimal stimulation position by rounding off the calculated standardized current value by the preset current resolution.

In step S530, the server 100 can calculate the total sum of the plurality of primarily-corrected current values and can determine whether the total sum of the calculated plurality of primarily-corrected current values is 0.

In step S540, in a case where it is determined that the total sum of the plurality of primarily-corrected current values is not 0, the server 100 can select at least one optimal stimulation position among the plurality of optimal stimulation positions based on the importance of each of the plurality of optimal stimulation positions. Herein, a method for setting the importance of each of the plurality of optimal stimulation positions can be implemented in the same or similar form as the method for setting the importance performed in step S430 (for example, a method based on the optimal stimulation position and the current intensity applied to the optimal stimulation position). However, the present invention is not limited thereto.

Herein, the server 100 can determine the number of the optimal stimulation positions selected according to the magnitude of the total sum of the plurality of primarily-corrected current values. For example, in a case where the magnitude of the total sum of the plurality of primarily-corrected current values is 4 (as the standardized current value, the real current value is 800 mA) and the preset current resolution is 1 (as the standardized current value, the real current value is 200 mA), the server 100 can select a total of four optimal stimulation positions in order to correct the current value applied to the optimal stimulation position by 200 mA which is the current resolution. However, the present invention is not limited thereto.

In various embodiments, the server 100 can sequentially select at least one optimal stimulation position in order from the optimal stimulation position having a low importance based on the importance of each of the plurality of optimal stimulation positions set according to the above scheme (the position of the optimal stimulation position and the current intensity applied to the optimal stimulation position). For example, the server 100 can sequentially select the optimal stimulation positions in order from the optimal stimulation position having the lowest current intensity applied to each of the plurality of optimal stimulation positions.

In various embodiments, the server 100 can determine a method for selecting at least one optimal stimulation position according to the importance setting standard for each of the plurality of optimal stimulation positions.

As an example, in a case where the importance setting standard is the position of the plurality of optimal stimulation positions, the server 100 can sequentially select optimal stimulation positions in order from the optimal stimulation position having a low importance based on the set importance.

On the other hand, in a case where the importance setting standard is the current intensity applied to each of the plurality of optimal stimulation positions, the server 100 can sequentially select the optimal stimulation positions in order from the optimal stimulation position having a high importance based on the set importance.

In a case where the importance setting standard is the current intensity, as the current intensity becomes lower, the importance becomes lower. Therefore, in a case where the optimal stimulation positions are sequentially selected in order from the optimal stimulation position having a low importance, the optimal stimulation positions are selected in order from the optimal stimulation position having a low current intensity. Since the current value applied to the optimal stimulation position selected in this manner has a relatively low value, in case where the current value is corrected by the current resolution, the current value becomes very small, and thus, the influence of the electric stimulation is almost eliminated or the applied the current value is set to 0 in some cases. As a result, there is no influence in applying the electric stimulation to the target point. On the other hand, in the case of the optimal stimulation position in which the importance is set to be high, since the applied the current value is large, even if correction is performed by adding or subtracting as much as a magnitude of the current resolution, there is no significant influence in applying the electric stimulation to the target point. In consideration of this point, the server 100 can sequentially select the optimal stimulation positions in order from the optimal stimulation position having an importance set to be high in a case where the importance setting standard is the current intensity.

In step S550, the server 100 can correct the current values (primarily-corrected current values) corresponding to the at least one optimal stimulation position selected through step S540 so that the total sum of the plurality of primarily-corrected current values become 0. For example, in a case where the magnitude of the total sum of the plurality of primarily-corrected current values is 800 mA and the preset current resolution is 200 mA, and a total of four optimal stimulation positions are selected based on the importance, the server 100 can secondarily correct the current values by decreasing each the current value applied to each of the four optimal stimulation positions by 200 mA so that the total sum of the plurality of primarily-corrected current values is 0.

In step S560, the server 100 calculates the current value to be applied to each of the plurality of optimal stimulation positions by multiplying the plurality of current values secondarily-corrected through step S550 by the preset current resolution and can provide the information on the optimal stimulation position combination including the information on the optimal stimulation position and the information on the current value to be applied to each optimal stimulation position through the third UI 70 by using the calculated the current value (for example, FIG. 18).

In step S570, in a case where it is determined that the total sum of the plurality of primarily-corrected current values is 0 at step S530, the server 100 can calculate the current value to be applied to each of the plurality of optimal stimulation positions by multiplying each of the plurality of primarily-corrected current values by the preset current resolution and can provide the information on the optimal stimulation position combination including information on the calculated the current value. Hereinafter, the method for designing the customized headgear for the subject by using the optimal stimulation position combination determined according to the above-described method by the server 100 will be described with reference to FIGS. 19 and 20.

Figure 19:
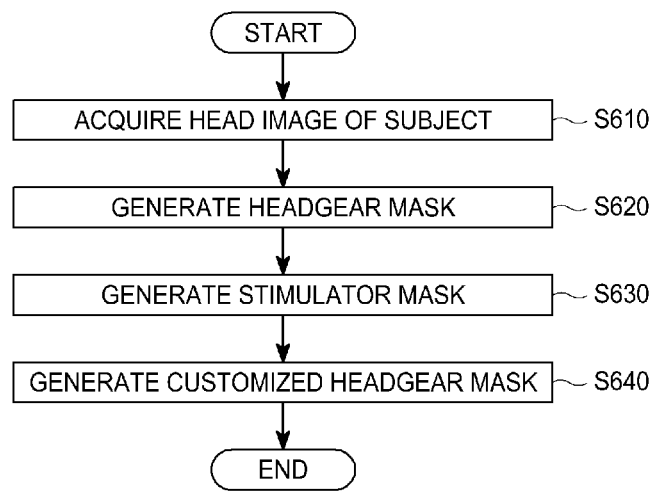
FIG. 19 is a flowchart of a method for designing a customized headgear for transcranial direct current stimulation according to another embodiment of the present invention.
Figure 20:
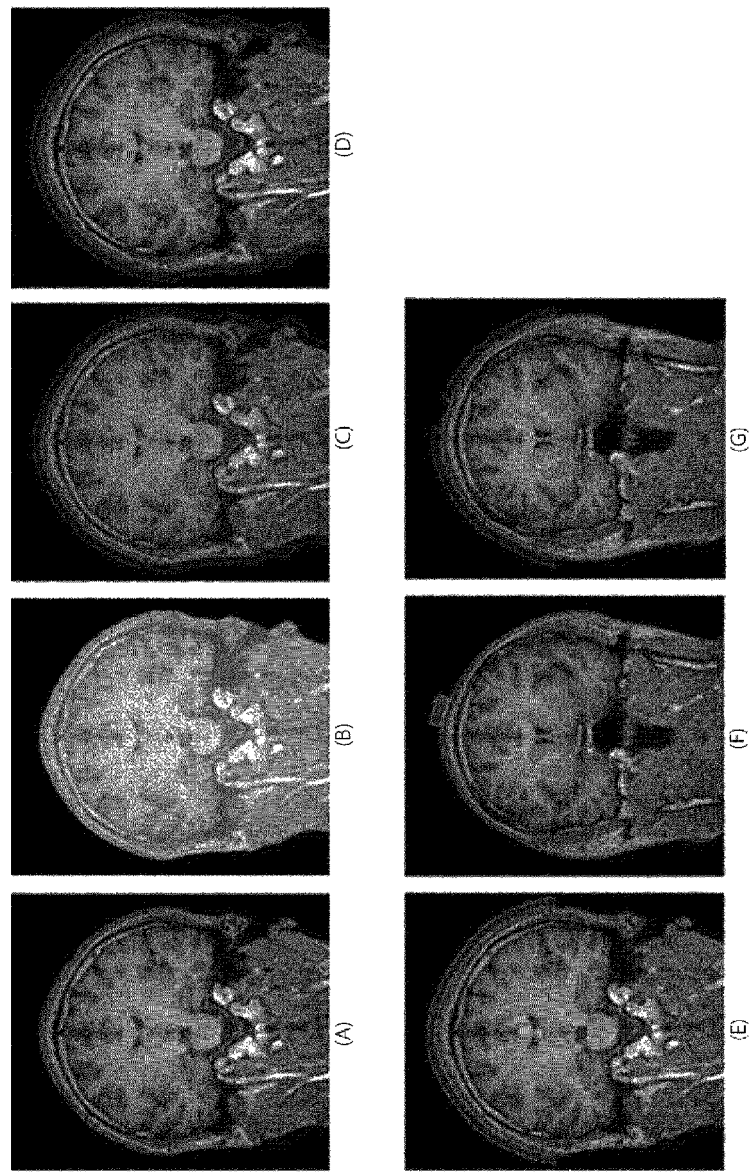
FIG. 20 is a diagram illustrating a process of generating a customized headgear mask for a subject according to a method for designing the customized headgear for transcranial direct current stimulation, according to various embodiments.

FIG. 19 is a flowchart of a method for designing a customized headgear for transcranial direct current stimulation according to another embodiment of the present invention.

Referring to FIG. 19, in step S610, the server 100 may acquire the head image of the subject. Herein, the head image of the subject may be a T1w MRI image as illustrated in FIG. 20A, but the present invention is not limited thereto, and various types of images such as MRI image (e.g., a T2w MRI image, a FLAIR MRI image, etc.) and a CT image may be applied.

In step S620, the server 100 may generate the headgear mask by using the head image of the subject acquired through step S610.

First, the server 100 may generate the head mask including the head information (for example, the size, shape, and the like of the head) by analyzing the head image of the subject obtained through step S610 as illustrated in FIG. 20B.

Thereafter, the server 100 may perform the image processing on the head mask, as illustrated in FIG. 20C. For example, the server 100 may perform a dilation operation on the head mask. In this case, the degree of the dilation operation performed by the server 100 may be determined based on the thickness of the customized headgear to be designed, but the present invention is not limited thereto.

Then, the server 100 may generate the headgear mask by performing the subtraction operation between the head mask (FIG. 20C) image-processed (dilation operation) and the non-image-processed head mask (FIG. 20B), as illustrated in FIG. 20D. Herein, the subtraction operation may be the logical subtraction operation of Boolean Operation (the operation that calculates the area vector of the upper mask (FIG. 20C) from which the lower mask (FIG. 20B) is removed), however, the present invention is not limited thereto.

In various embodiments, the server 100 may reject at least a partial area of the headgear mask (FIG. 20D).

First, the server 100 may set the plurality of reference points on the headgear mask (FIG. 20D) and may reject at least a partial area of the headgear mask by using the set plurality of reference points.

For example, as illustrated in FIG. 20E, the server 100 may provide four reference points corresponding to the nasion, the inion, the left pre-auricular, and the right pre-auricular of the subject on the headgear mask (for example, Nz corresponding to the nasion, Iz corresponding to the inion, LPA corresponding to the left pre-auricular, and RPA corresponding to the right pre-auricular among the plurality of stimulation positions according to the 10-20 system), may segment the headgear mask into the upper area and the lower area based on the plane including four set reference points, and may reject the segmented lower area from the headgear mask (FIG. 20D).

That is, in order for the subject to more easily wear the customized headgear manufactured through the headgear mask and in order to implement the customized headgear in the form that covers only the forehead and the portions above both ears of the subject, the server 100 may designate four landmarks (for example, four reference points corresponding to the nasion, the inion, the left pre-auricular, and the right pre-auricular) and may reject the portion below the forehead, the portions below both ears, and the portion below the inion based on the four designated landmarks.

In addition, when the specific area needs to be opened due to the injury such as the scalp disease or the wound on the head of the subject, the server 100 may set the position corresponding to the specific area to be opened as a reference point and may reject the area having a predetermined radius centered at the set reference point from the headgear mask. However, the present invention is not limited thereto, and when there is an injury to the head of the subject, the server 100 may set the size and shape of the area to be removed from the headgear mask according to the property of the injury (for example, the type, shape, size, or the like of the injury), and thus, may reject the set area from the headgear mask.

In addition, the server 100 may generate two holes (first hole) by removing at least a partial area adjacent to each of the two reference points on the headgear mask by using two reference points corresponding to the left pre-auricular and the right pre-auricular among the plurality of reference points. Herein, the two first holes may be holes into which a chin strap for fixing the customized headgear manufactured by using a customized headgear mask generated through step S640 to be described later and the chin of the subject wearing the customized headgear is inserted, and the size of the first hole may be set to the size in which the chin strap can be inserted, but the present invention is not limited thereto.

In addition, when the wire (for example, the electric wire connected to supply the power supplied to the transcranial direct current stimulation (tDCS) device to the electrode) is connected to the electrode of the transcranial direct current stimulation (tDCS) device used to apply the electrical stimulation to the brain of the subject, the server 100 may generate one or more holes (second holes) by removing at least a partial area of the headgear mask. Herein, the one or more second holes may be inserted with the wire of the electrode attached to the head of the subject in order to apply the electrical stimulation to the preset target point, and the inserted wire of the electrode may be exposed from the inside of the customized headgear to the outside, but the present invention is not limited thereto.

In step S630, the server 100 may generate the stimulator mask by using the optimal stimulation position combination for applying the electrical stimulation to the preset target point.

Herein, as illustrated in FIG. 20F, the stimulator mask may be implemented in a form of a mask having a size of the electrodes attached to each optimal stimulation position only in the area corresponding to each of the plurality of optimal stimulation positions included in the optimal stimulation position combination, but the present invention is not limited thereto.

In addition, herein, the method for determining the optimal stimulation position for applying the electrical stimulation to the preset target point performed by the server 100 is implemented to be the same as or similar to the method for determining the optimal stimulation position for applying the electrical stimulation to the preset target point described with reference to FIGS. 3 to 18, but the present invention is not limited thereto.

In various embodiments, when there are a plurality of the target points for applying the electrical stimulation to the brain of the subject, the server 100 may determine the plurality of optimal stimulation position combinations for applying the electrical stimulation to each of the plurality of target points, may generate the plurality of stimulator masks corresponding to each of the plurality of determined optimal stimulation position combinations, and may generate one stimulator mask by combining the plurality of generated stimulator masks.

First, when the preset target point in the brain of the subject includes the first target point and the second target point, the server 100 may individually determine the first optimal stimulation position combination for the first target point and the second optimal stimulation position combination for the second target point.

Thereafter, the server 100 may generate one stimulator mask by combining (for example, performing logical union operation of Boolean operation) the stimulator mask according to the first optimal stimulation position combination and the stimulator mask according to the second optimal stimulation position combination. For example, when the first optimal stimulation position combination includes the first optimal stimulation position and the second optimal stimulation position, and the second optimal stimulation position combination includes the third optimal stimulation position and the fourth optimal stimulation position, the server 100 may generate a stimulator mask corresponding to the first optimal stimulation position, the second optimal stimulation position, the third optimal stimulation position, and the fourth optimal stimulation position. In addition, when the first optimum stimulation position combination includes the first optimum stimulation position and the second optimum stimulation position, and the second optimum stimulation position combination includes the first optimum stimulation position and the third optimum stimulation position, the server 100 may generate a stimulator mask corresponding to the first optimum stimulation position, the second optimal stimulation position, and the third optimal stimulation position.

In step S640, the server 100 may generate the customized headgear mask by performing the subtraction operation between the headgear mask generated in step S620 and the stimulator mask generated in step S630. Herein, the subtraction operation may be the logical subtraction operation of the Boolean operation, but the present invention is not limited thereto.

That is, as illustrated in FIG. 20G, the server 100 may generate the customized headgear mask for the subject in consideration of the head of the subject and may generate the customized headgear mask in which the area corresponding to the optimal stimulation position is removed from the headgear mask by performing the subtraction operation between the headgear mask and the stimulator mask. Accordingly, the electrodes through the open area of the customized headgear are attached to the subject wearing the customized headgear manufactured by using the customized headgear mask, and thus, the electrodes may be accurately attached to each of the plurality of optimal stimulation positions, so that there is an advantage in that electrical stimulation may be accurately applied to the preset target point of the brain of the subject.

In addition, even when the electrical stimulation is repeatedly applied, the electrode is attached through the open area of the customized headgear, so that there is an advantage in that the same effect may be continuously derived by accurately attaching the electrode to the same position.

In various embodiments, the server 100 may manufacture the customized headgear for the subject by three-dimensional printing the customized headgear mask through a three-dimensional printer. For example, the server 100 may perform data conversion in a form that the customized headgear mask can be output with a three-dimensional printer such as in a three-dimensional polygonal grid structure (for example, a three-dimensional triangular grid structure) and may manufacture the customized headgear for the subject by three-dimensionally printing the data-converted, customized headgear mask with the three-dimensional printer separately provided. However, the present invention is not limited thereto. Herein, the server 100 is described as converting the customized headgear mask into the three-dimensional polygonal grid structure for three-dimensionally printing, but it is only the example and the present invention is not limited thereto. The server 100 may determine the data form of the customized headgear mask depending on the properties of the three-dimensional printer to be used. For example, when the server 100 uses the three-dimensional printer capable of outputting the customized headgear mask itself, the server 100 may manufacture the customized headgear mask by three-dimensionally printing the customized headgear mask without the separate data conversion process.

Figure 21:
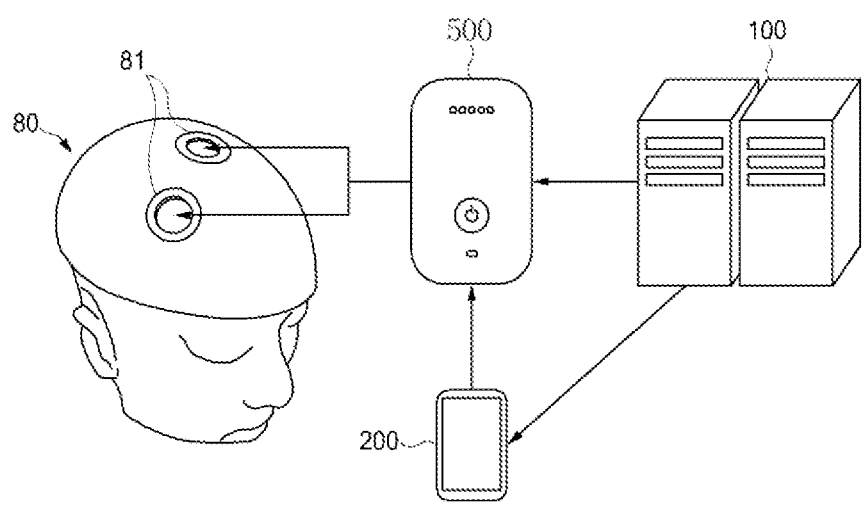
FIG. 21 is a diagram illustrating a process of performing transcranial direct current stimulation using the customized headgear manufactured through the customized headgear mask according to various embodiments of the present invention.

In various embodiments, the server 100 may apply the electrical stimulation to the preset target point in the brain of the subject by using the customized headgear. For example, referring to FIG. 21, the server 100 may manufacture the customized headgear 80 provided with the holes 81 in the area corresponding to the optimal stimulation position by using the customized headgear mask generated according to the above-described method (for example, three-dimensional printing).

Thereafter, the subject may wear the customized headgear 80 manufactured according to the above-described method, and one or more electrodes included in the transcranial direct current stimulation (tDCS) device 500 are attached to the head of the subject by being inserted into the holes 81 corresponding to the optimal stimulation position, so that the electrodes may be accurately attached to the optimal stimulation position determined to apply the electrical stimulation to the preset target point.

Thereafter, the operation of applying the current through one or more electrodes may be performed according to any one control command among the control command input from the server 100 (for example, the control command to operate according to the pre-determined optimal stimulation position combination in response to the electrode being attached to the subject), the control command input through the user terminal 200 (for example, the operation command of the transcranial direct current stimulation (tDCS) device 500 input through the UI), and the control command input through the transcranial direct current stimulation (tDCS) device 500 itself (for example, on/off control command of the operation), and the preset target point in the brain of the subject can be accurately stimulated by accurately applying the electrical stimulation to the optimal stimulation position of the subject.

The above-described method for designing the customized headgear for transcranial direct current stimulation is described with reference to the flowchart illustrated in the drawings. For a simple description, the optimal stimulation position combination determination method using the preset guide system has been illustrated and described as a series of blocks, but the present invention is not limited to the order of the blocks, and some blocks may be performed in an order different from or simultaneously with those illustrated and operated in this specification. In addition, the embodiments can be performed in a state where new blocks not described in the present specification and the drawings can be added, or some blocks can be deleted or changed.

In the above, embodiments of the present invention have been described with reference to the accompanying drawings, but the ordinarily skilled in the art to which the present invention belongs can understand that the present invention can be carried out in other specific forms without changing technical spirit or essential features. Therefore, it should be understood that the embodiments described above are illustrative in all respects and are not restrictive.

What is claimed is:

1. A method for designing a customized headgear for transcranial direct current stimulation performed by a computing device and applying electrical stimulation to a preset target point in a brain of a subject, the method comprising:
acquiring a head image of the subject;
generating a headgear mask by using the acquired head image;
generating a stimulator mask by using an optimal stimulation position combination for applying the electrical stimulation to the preset target point; and
generating a customized headgear mask for the subject by performing a subtraction operation between the generated headgear mask and the generated stimulator mask,
wherein the generating the stimulator mask includes:
simulating electrical stimulation for the brain of the subject by using a plurality of stimulation positions according to a preset guide system;
determining the optimal stimulation position combination by using a simulation result of the electrical stimulation; and
generating the stimulator mask based on a plurality of optimal stimulation positions included in the determined optimal stimulation position combination, and
wherein simulating electrical stimulation for the brain of the subject includes:
acquiring a Magnetic Resonance Imaging (MRI) image of the brain of the subject;
segmenting the acquired MRI image into a plurality of regions;
generating a three-dimensional brain image by using the MRI image segmented into the plurality of regions;
generating a three-dimensional brain map configured with a plurality of meshes based on an attribute of each of the plurality of regions included in the generated three-dimensional brain image; and
simulating the electric stimulation by using the plurality of stimulation positions based on the generated three-dimensional brain map.

2. The method according to claim 1, wherein the generating the headgear mask includes:
generating a head mask for the subject by using the acquired head image; and
generating the headgear mask by performing image processing on the generated head mask and performing a subtraction operation between the image-processed head mask and the generated head mask.

3. The method according to claim 1, wherein the generating the headgear mask includes:
setting a plurality of reference points on the generated headgear mask; and
removing at least the partial area of the generated headgear mask by using the plurality of set reference points.

4. The method according to claim 3,
wherein the plurality of reference points include four reference points corresponding to a nasion, an inion, a left pre-auricular, and a right pre-auricular of the subject, and
wherein the removing at least the partial area of the generated headgear mask includes segmenting the generated headgear mask into an upper area and a lower area based on a plane including the four reference points and removing the segmented lower area from the generated headgear mask.

5. The method according to claim 3,
wherein the plurality of reference points includes two reference points corresponding to a left pre-auricular and a right pre-auricular, and
wherein the removing at least the partial area of the generated headgear mask includes generating two holes by removing at least a partial area adjacent to the two reference points, and
wherein a chin strap for fixing a customized headgear manufactured using the generated customized headgear mask and a chin of the subject wearing the customized headgear is inserted into the generated two holes.

6. The method according to claim 1, wherein the generating the headgear mask includes generating one or more holes by removing at least the partial area of the generated headgear mask, and
wherein a line of an electrode attached to a head of the subject in order to apply the electrical stimulation to the preset target point is inserted into the generated holes and the inserted line of the electrode is exposed from an inside to an outside of the customized headgear manufactured by using the generated customized headgear mask through the generated holes.

7. The method according to claim 1,
wherein the determining the optimal stimulation position combination includes determining a plurality of the optimal stimulation position combinations for applying the electrical stimulation to the plurality of target points when there are a plurality of the preset target points, and
wherein the generating the stimulator masks corresponding to the plurality of optimal stimulation positions includes generating a plurality of the stimulator masks corresponding to the determined plurality of optimal stimulation position combinations and generating one stimulator mask by combining the generated plurality of stimulator masks.

8. The method according to claim 1,
wherein the determining the optimal stimulation position combination includes:
setting a maximum number of stimulation positions to which the electrical stimulation to the preset target point is applied;
correcting the determined optimal stimulation position combination by comparing the number of optimal stimulation positions included in the determined optimal stimulation position combination with the set maximum number of stimulation positions, and
wherein the generating the stimulator masks corresponding to each of the plurality of optimal stimulation positions includes generating the stimulator masks corresponding to each of the plurality of optimal stimulation positions included in the corrected optimal stimulation position combination.

9. The method according to claim 1, further comprising:
converting the generated customized headgear mask into a three-dimensional polygonal grid structure; and
manufacturing the customized headgear for the subject by three-dimensionally printing the customized headgear mask converted into the three-dimensional polygonal grid structure.

10. A server for designing a customized headgear for transcranial direct current stimulation, the server comprising:
- a processor;
- a network interface;
- a memory; and
- a computer program loaded on the memory and executed by the processor,
- wherein the computer program includes:
  - an instruction for acquiring a head image of a subject;
  - an instruction for generating a headgear mask by using the acquired head image;
  - an instruction for generating a stimulator mask by using an optimal stimulation position combination for applying electrical stimulation to a preset target point in a brain of the subject; and
  - an instruction for generating a customized headgear mask for the subject by performing a subtraction operation between the generated headgear mask and the generated stimulator mask,
- wherein the instruction for generating a stimulator mask includes:
  - an instruction for simulating electrical stimulation for the brain of the subject by using a plurality of stimulation positions according to a preset guide system;
  - an instruction for determining the optimal stimulation position combination by using a simulation result of the electrical stimulation; and
  - an instruction for generating the stimulator mask based on a plurality of optimal stimulation positions included in the determined optimal stimulation position combination, and
- wherein the instruction for simulating electrical stimulation for the brain of the subject includes:
  - an instruction for acquiring a Magnetic Resonance Imaging (MRI) image of the brain of the subject;
  - an instruction for segmenting the acquired MRI image into a plurality of regions;
  - an instruction for generating a three-dimensional brain image by using the MRI image segmented into the plurality of regions;
  - an instruction for generating a three-dimensional brain map configured with a plurality of meshes based on an attribute of each of the plurality of regions included in the generated three-dimensional brain image; and
  - an instruction for simulating the electric stimulation by using the plurality of stimulation positions based on the generated three-dimensional brain map.

11. A computer program recorded on a computer-readable recording medium, combined with a computing device, the computer program causing the computing device to execute:
- acquiring a head image of a subject;
- generating a headgear mask by using the acquired head image;
- generating a simulator mask by using an optimal stimulation position combination for applying electrical stimulation to a preset target point in a brain of the subject; and
- generating a customized headgear mask for the subject by performing a subtraction operation between the generated headgear mask and the generated stimulator mask,
- wherein the generated stimulator mask includes:
- simulating electrical stimulation for the brain of the subject by using a plurality of stimulation positions according to a preset guide system;
- determining the optimal stimulation position combination by using a simulation result of the electrical stimulation; and
- generating the stimulator mask based on a plurality of optimal stimulation positions included in the determined optimal stimulation position combination, and
- wherein simulating electrical stimulation for the brain of the subject includes:
  - acquiring a Magnetic Resonance Imaging (MRI) image of the brain of the subject;
  - segmenting the acquired MRI image into a plurality of regions;
  - generating a three-dimensional brain image by using the MRI image segmented into the plurality of regions;
  - generating a three-dimensional brain map configured with a plurality of meshes based on an attribute of each of the plurality of regions included in the generated three-dimensional brain image; and
  - simulating the electric stimulation by using the plurality of stimulation positions based on the generated three-dimensional brain map.

* * * * *